(12) United States Patent
Fernandez Prada et al.

(10) Patent No.: US 11,419,521 B2
(45) Date of Patent: Aug. 23, 2022

(54) SENSOR DEVICE AND CARRIERS

(71) Applicant: JANSSEN PHARMACEUTICA NV, Beerse (BE)

(72) Inventors: Kenneth David Fernandez Prada, Ambler, PA (US); Ivan Avila, King of Prussia, PA (US)

(73) Assignee: Janssen Pharmaceutica NV, Beerse (BE)

( * ) Notice: Subject to any disclaimer, the term of this patent is extended or adjusted under 35 U.S.C. 154(b) by 1035 days.

(21) Appl. No.: 15/416,511

(22) Filed: Jan. 26, 2017

(65) Prior Publication Data

US 2017/0215766 A1 Aug. 3, 2017

Related U.S. Application Data

(60) Provisional application No. 62/288,681, filed on Jan. 29, 2016.

(51) Int. Cl.
*A61B 5/00* (2006.01)
*A61B 5/107* (2006.01)
(Continued)

(52) U.S. Cl.
CPC .......... *A61B 5/1072* (2013.01); *A61B 5/0015* (2013.01); *A61B 5/0082* (2013.01);
(Continued)

(58) Field of Classification Search
CPC ..... A61B 5/1072; A61B 5/107; A61B 5/1116; A61B 5/0015; A61B 5/1121; A61B 5/11; A61B 5/1114
See application file for complete search history.

(56) References Cited

U.S. PATENT DOCUMENTS 4,485,825 A * 12/1984 Domjan ............... A61B 5/1071
33/352
4,665,928 A * 5/1987 Linial .................. A61B 5/1121
482/1
(Continued)

FOREIGN PATENT DOCUMENTS

| EP | 2141632 A2 | 1/2010 |
| JP | 2016531681 A * | 8/2013 |
| WO | WO 2009/053671 A1 | 4/2009 |

OTHER PUBLICATIONS

Borman et al., "Ultrasound detection of entheseal insertions in the foot of patients with spondyloarthropathy", Clinical Rheumatology; Journal of the International League of Associations for Rheumatology, May 1, 2006, vol. 25, No. 3, 373-377.

*Primary Examiner* — Jennifer Pitrak McDonald
*Assistant Examiner* — Sana Sahand
(74) *Attorney, Agent, or Firm* — BakerHostetler

(57) ABSTRACT

Disclosed herein are systems comprising sensor devices that may be affixed to a patient and used to perform clinical measurements such as measurements for calculating a BASMI score. A first sensor device is configured to be successively attached to each of a wrist carrier, an ankle carrier, and a headset carrier. The carriers are attached to, or positioned next to, the relevant portion of the patient's body in order to perform particular measurements relating to generating a BASMI score. As the patient performs the routine of motions associated with a particular BASMI measurement, the sensor device records the measurements and communicates the measurements to a user computing device. A second sensor device is configured to be applied to the patient's torso and an additional measurement of (Continued)

patient flexibility taken and communicated to the user computing device. The user computing device generates a BASMI score from the recorded measurements.

23 Claims, 25 Drawing Sheets

(51) Int. Cl.
*A61B 5/11* (2006.01)
*G16H 50/30* (2018.01)
*G16H 40/63* (2018.01)
*G16Z 99/00* (2019.01)
*A61B 8/08* (2006.01)

(52) U.S. Cl.
CPC .......... *A61B 5/1079* (2013.01); *A61B 5/1114* (2013.01); *A61B 5/1116* (2013.01); *A61B 5/1121* (2013.01); *A61B 5/407* (2013.01); *A61B 5/4566* (2013.01); *A61B 5/6801* (2013.01); *A61B 5/6814* (2013.01); *A61B 5/6823* (2013.01); *A61B 5/6824* (2013.01); *A61B 5/6825* (2013.01); *A61B 5/6829* (2013.01); *A61B 5/6831* (2013.01); *A61B 5/7278* (2013.01); *A61B 8/08* (2013.01); *G16H 40/63* (2018.01); *G16H 50/30* (2018.01); *G16Z 99/00* (2019.02)

(56) References Cited

U.S. PATENT DOCUMENTS

| | | | | |
|---|---|---|---|---|
| 6,487,906 B1* | 12/2002 | Hock | .................... | A61B 5/1126 |
| | | | | 73/379.01 |
| 2008/0287770 A1* | 11/2008 | Kurzweil | .................. | A61B 5/08 |
| | | | | 600/388 |
| 2009/0322763 A1* | 12/2009 | Bang | .................. | G06K 9/00342 |
| | | | | 345/474 |
| 2012/0179020 A1* | 7/2012 | Wekell | .................. | A61B 5/6828 |
| | | | | 600/384 |
| 2013/0023747 A1* | 1/2013 | Karo | .................... | A61B 5/1072 |
| | | | | 600/384 |
| 2013/0303286 A1* | 11/2013 | Ferguson | .............. | A61B 5/1127 |
| | | | | 463/37 |
| 2015/0087995 A1* | 3/2015 | Murai | .................... | A61B 5/684 |
| | | | | 600/473 |
| 2016/0198995 A1* | 7/2016 | Yeung | .................. | A61B 5/1128 |
| | | | | 600/595 |
| 2017/0136296 A1* | 5/2017 | Barrera | ................ | G09B 19/003 |
| 2017/0164876 A1* | 6/2017 | Hyde | .................. | A61B 5/7278 |

* cited by examiner

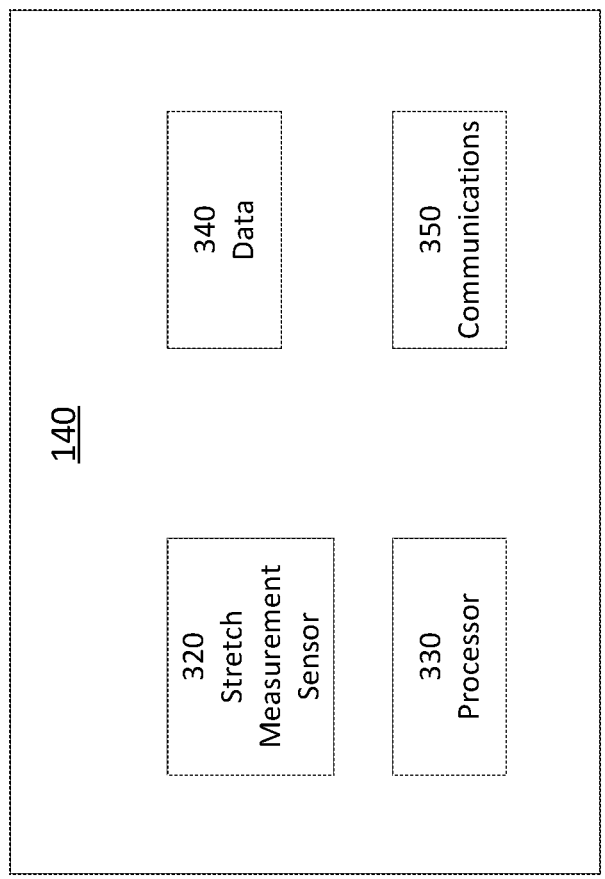

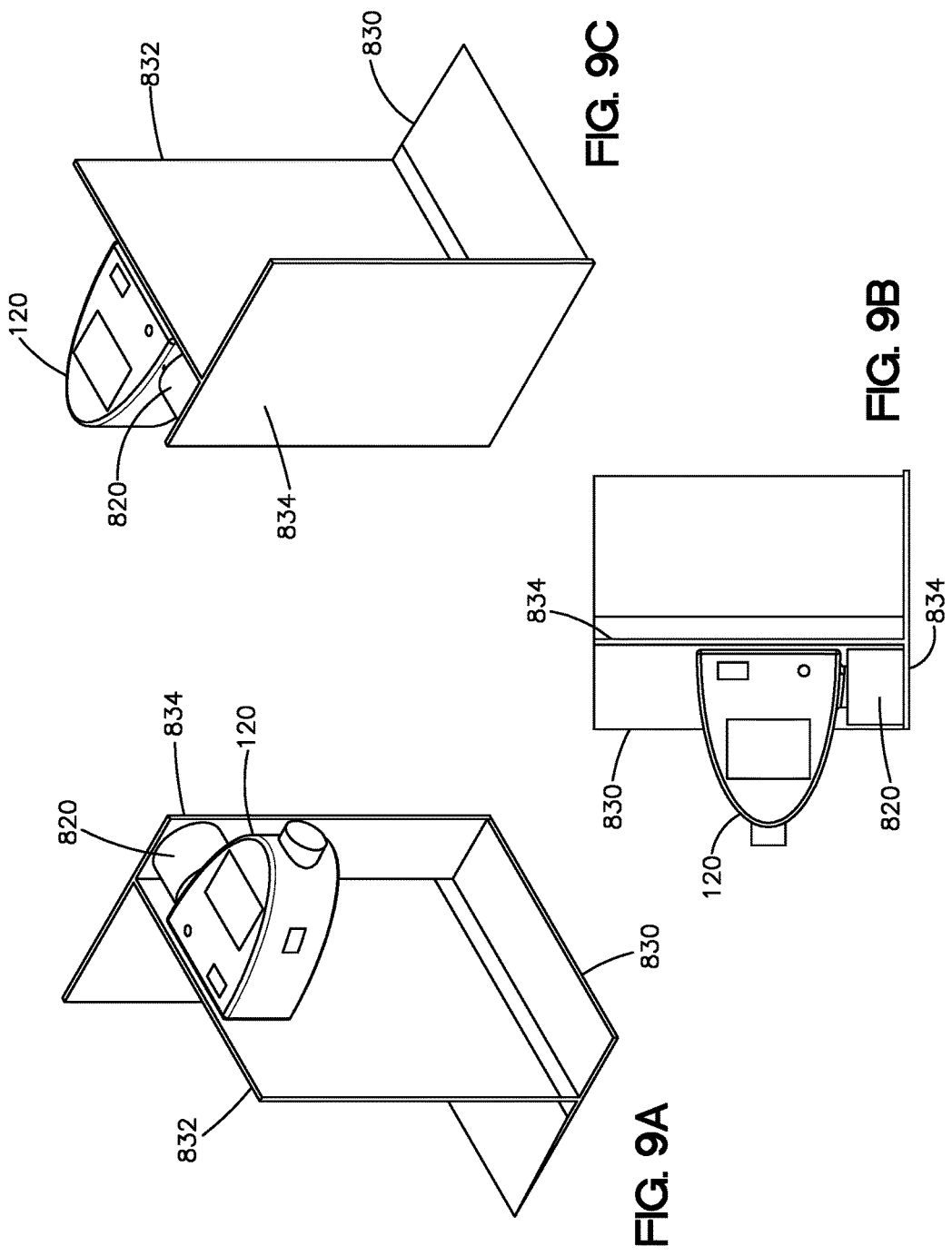

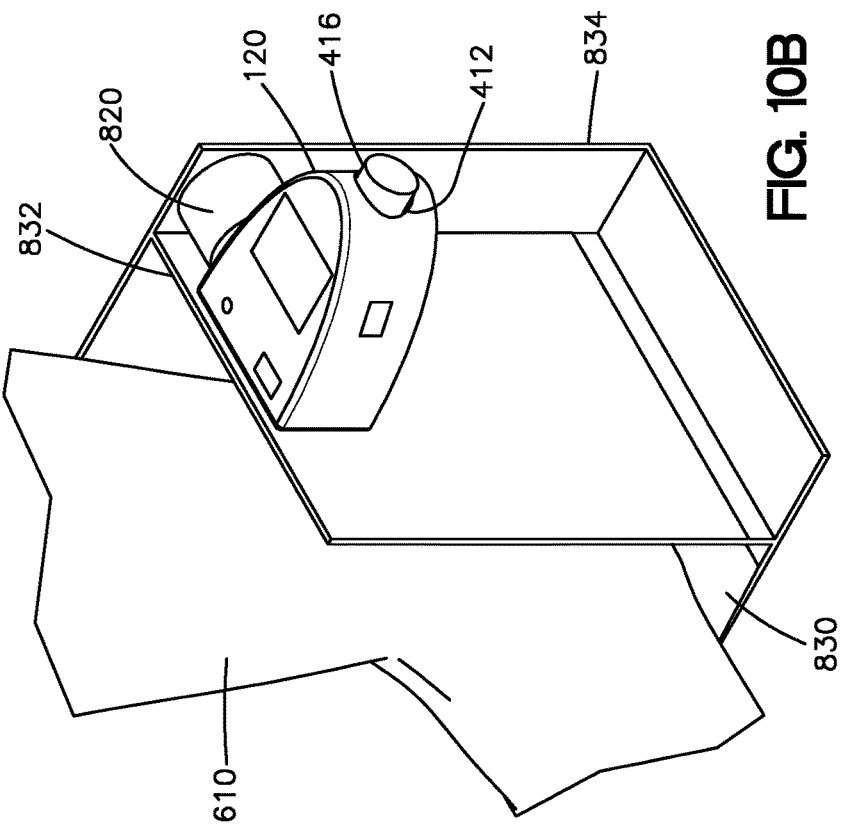
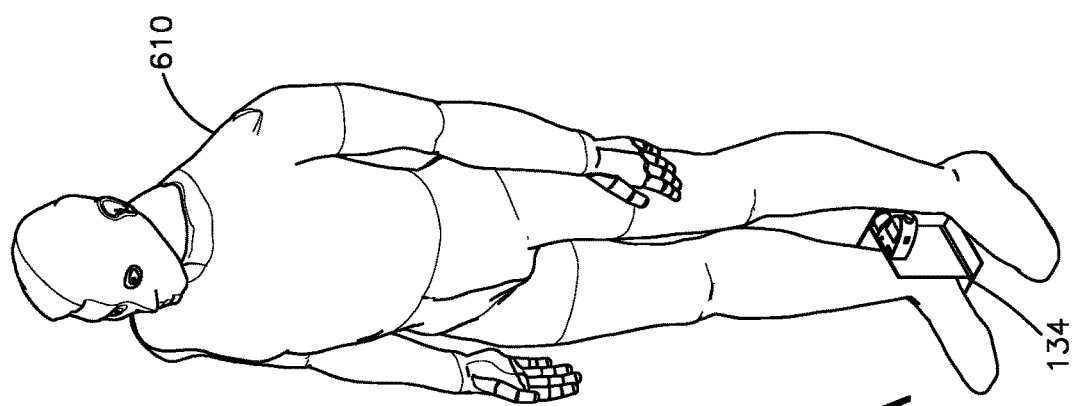
FIG. 10B
FIG. 10A

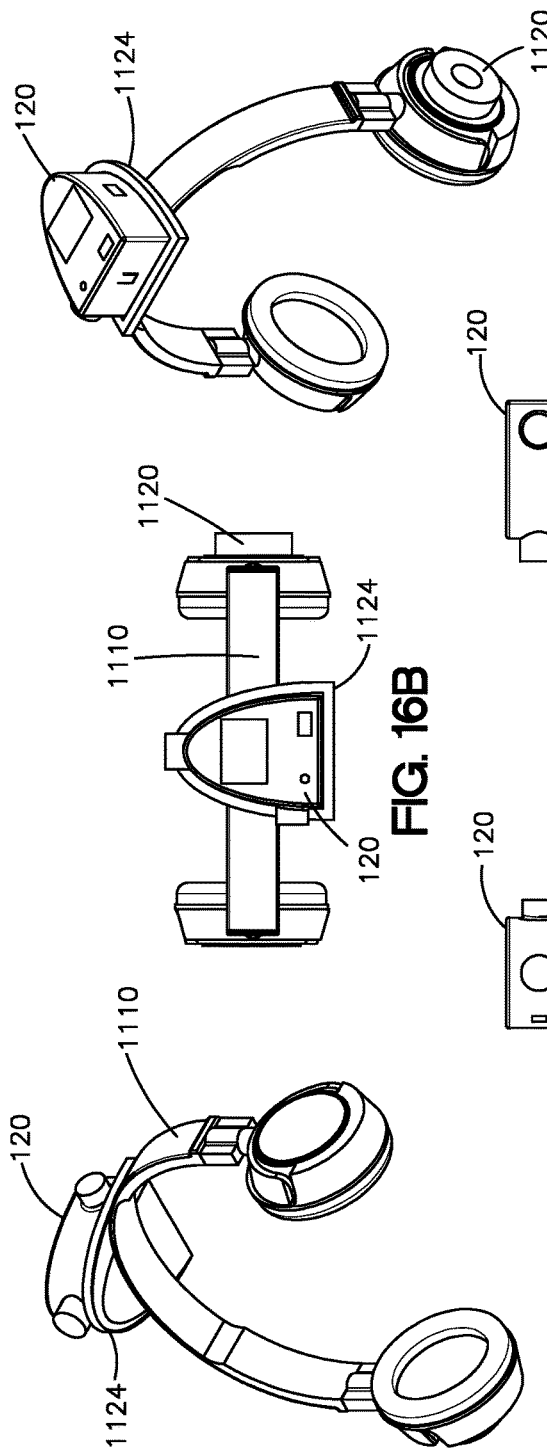

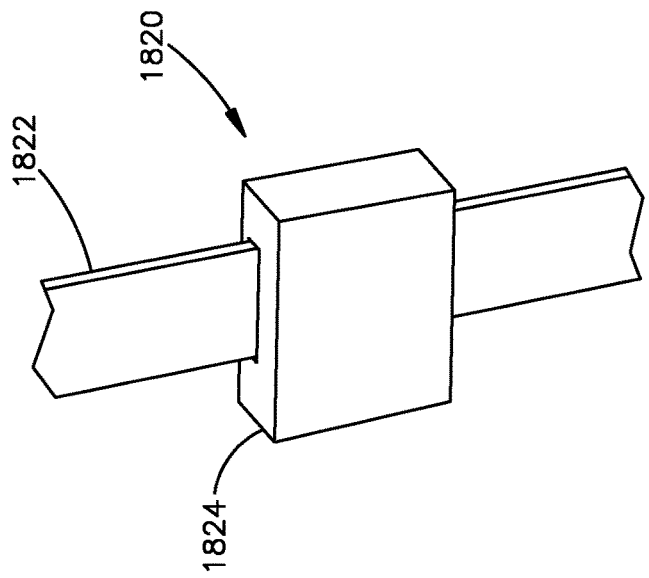
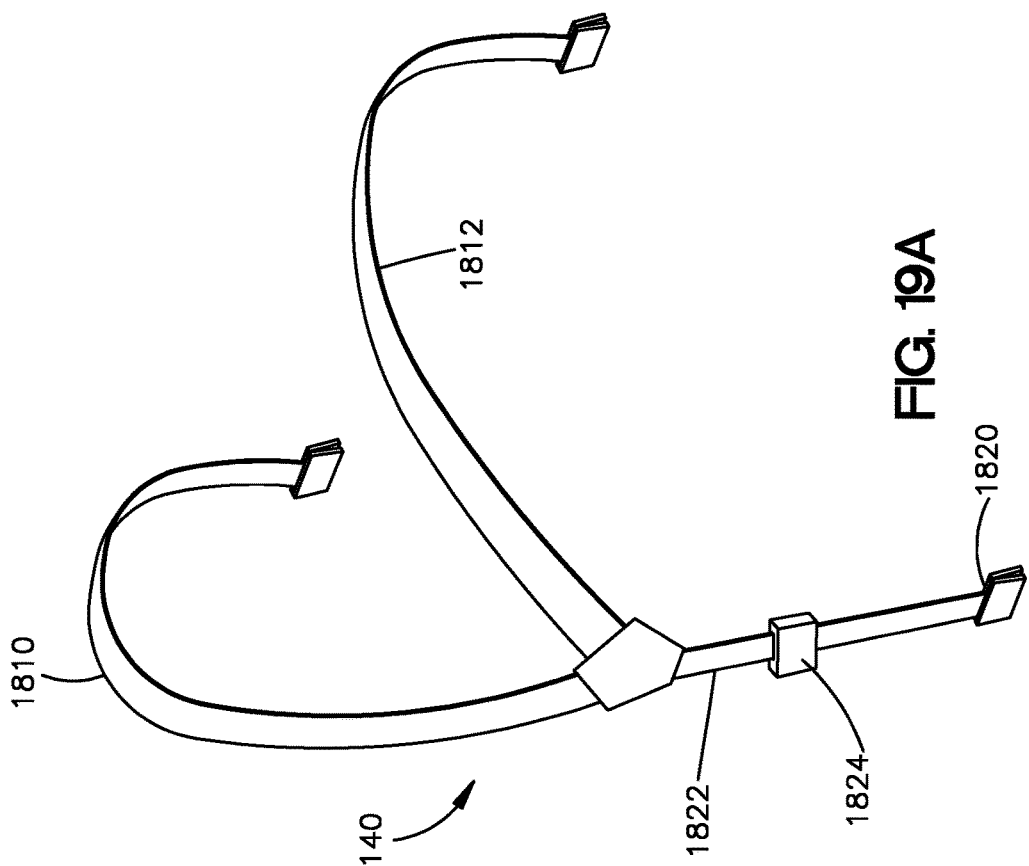
FIG. 19B
FIG. 19A

SENSOR DEVICE AND CARRIERS

CROSS-REFERENCE TO RELATED APPLICATIONS

This application claims priority to U.S. Patent Application Ser. No. 62/288,681, filed Jan. 29, 2016, the disclosure of which is hereby incorporated by reference as if set forth in its entirety herein.

BACKGROUND

Tracking of physical disease in humans often involves performing physical measurements of a patient's body. For example, tracking of a medical condition known as ankylosing spondylitis involves taking various measurements of body flexibility. Ankylosing spondylitis is a condition that primarily impacts the spine. The condition is caused by inflammation of spinal vertebrae which, over time, often results in the vertebrae becoming fused together. Affected persons suffer from chronic pain and reduced flexibility.

Development of ankylosing spondylitis may be tracked using a series of clinical measurements relating to the flexibility of the spine. For example, a series of five defined measurements may be taken, scores generated for each measurement, and a composite score derived from the measurement scores. The scores for each measurement and the composite score may be generated using any of several scoring methodologies or indexes such as, for example, the Bath Ankylosing Spondylitis Metrology Index (BASMI). The composite score provides an indication of the development of the disease.

The measurements used in generating a score require the patient to bend in various prescribed manners while measuring the degree of movement. The measurements are taken manually by a health care professional such as a physical therapist, nurse, or doctor. Accordingly, a special trip to a medical facility such as a rehabilitation or doctor's office is required for the measurements to be collected. Because patients often lack the time or ability to make frequent visits to a doctor's office, the measurements are typically taken less frequently than desired for optimal tracking of the disease.

SUMMARY

Disclosed herein are systems comprising sensor devices that may be affixed to a patient and used to perform clinical measurements. The measurements may be for any suitable purpose such as, for example, tracking the progress of disease such ankylosing spondylitis or tracking a patient's recovery from surgery.

In an example embodiment, a first sensor device comprises one or more electronic sensors that are programmed to measure distance and rotation. The sensors may be any that are suitable for taking the desired measurements. In an example embodiment, the sensor device may comprise one or more distance sensors including an ultrasonic rangefinder that is programmed to measure distance using an ultrasonic beam, and a proximity sensor that is programmed to measure distance using a light beam. In an example embodiment, inertial sensors may be programmed to measure motion of the sensor in free space.

The sensor devices are configured to be attached or affixed to various carriers which are then attached to or aligned with a patient's body part. As the patient moves through a series of prescribed motions, the sensor device measures the movements.

In an example embodiment, a first carrier is configured to be affixed to a wrist or arm carrier. This first carrier, which may be referred to as a wrist carrier, is configured to have the first sensor device affixed thereto and then to be attached to a patient's arm or hand. A distance sensor comprised in the first sensor device is positioned to measure the distance between the sensor and the surface on which the patient is standing. Using a user computing device such as, for example, a smart phone, tablet, or other computing device that is configured to wirelessly communicate with the sensor device, the patient requests that the sensor device capture the measurements for a movement that is sometimes referred to as a lumbar side flexion. As the patient bends sideways with the first sensor device affixed to his or her arm with the wrist carrier, the first sensor device measures the change in distance resulting from the patient's side flexion.

The first sensor device is configured to be affixed to a second carrier that is configured to measure the internalleolar distance, which generally refers to the distance between the patient's ankles when spread apart to the greatest extent possible. The second carrier, which may be referred to as the ankle carrier, comprises a frame that is formed so that it can be positioned adjacent to the patient's ankle. When the first sensor device is affixed to the ankle carrier and the ankle carrier positioned adjacent to the patient's ankle, the first sensor device, and in particular, a distance sensor within the first sensor device is positioned to measure the distance between the patient's ankle. Using the user computing device, the patient requests that the sensor device capture measurements of the intermalleolar distance. When the patient spreads his or her legs to the greatest extent possible, the sensor device measures the distance between the first sensor device and the opposing ankle area. The first sensor device records the measurements and communicates the measurements to the user computing device that initiated the process.

The first sensor device is further configured to be affixed to a third carrier that is used for measuring tragus to wall distance and cervical rotation. The third carrier, which may be referred to as the headset carrier, comprises a harness configured to be positioned on a patient's head. In an example embodiment, the headset carrier is formed in a generally arcuate shape and comprises at least two connectors configured to be used in affixing the first sensor device to the headset carrier in two different configurations. A first connector is formed proximate an area that, when the headset carrier is positioned on the patient's head, is positioned proximate the patient's ear. When the first sensor device is affixed to the headset carrier using this first connector on the headset carrier, the first sensor device is positioned to measure the distance between the first sensor device and a wall against which the patient stands. This is sometimes referred to as the tragus-to-wall distance. Using the user computing device, the patient request that the sensor device capture measurements of the tragus-to-wall distance. When the patient stands with his or her back to the wall and moves his or her chin inward as much as possible, the first sensor device is configured to measure the distance between the sensor device and the wall. The sensor records the measurements and communicates the measurements to the user computing device that initiated the process.

A second connector of the headset carrier is formed proximate an area that when the headset carrier is positioned on the patient's head, the second connector is positioned proximate the crown or top of the patient's head. When the sensor device is affixed to the headset carrier using this second connector on the headset carrier, the sensor device is positioned to measure the rotation of the patient's head. Using the smart phone, tablet, or other computing device that is configured to wirelessly communicate with the sensor device, the patient request that the sensor device capture measurements of the cervical rotation. When the patient rotates or turns their head from side to side to the greatest extent possible, the sensor device measures the degree of rotation. The sensor records the measurements and communicates the measurements to the smart phone or tablet that initiated the process.

According to another aspect of the disclosed systems, a second sensor device is employed to collect measurements relating to the amount that the patient's lumbar area increases in length when the patient flexes forward from the waist. This is sometimes referred to as the lumbar flexion measurement. The second sensor device has a configuration similar to a set of suspenders and, therefore, may be referred to herein as the suspender sensor system. The suspender sensor system comprises a first band configured to be applied over a patient's first shoulder and affixed at one end to a garment proximate the patient's waist. The suspender sensor system also comprises a second band configured to be applied over the patient's second shoulder and affixed at a first end to a garment proximate the patient's waist. The two bands are coupled at their second ends to a third band. The third band comprises at least a portion that is made of a flexible material and has a sensor integrated therewith. An end of the third band is configured to be connected to a garment at the patient's waist. When a patient applies or attaches the suspender sensor system to his or her torso, the first two bands are attached to a garment on the front of the patient's body and the bands extend over the patient's shoulders. The third band extends down the patient's back is attached at an end to a garment at the patient's waist. Using the user computing device, the patient requests that the sensor device capture measurements associated with a lumbar flexion. When the patient bends at his or her waist with knees fully extended, the suspender sensor device measures the amount that the third band expands. The suspender sensor device records the measurements and communicates the measurements to the smart phone or tablet that initiated the process.

In an example embodiment, as the user computing device receives the measurement data, it stores the data and generates individual scores for each of the measurements. In an example scenario wherein the collected measurement data relates to tracking ankylosing spondylitis, the scores may be based upon where each of the measurements falls within an established set of intervals defined by the BASMI scoring regimen. In such a scenario, the user computing device generates a composite BASMI score from the scores generated for each of the individual measurements. The BASMI score is typically a number from 0 to 10. The higher the BASMI score, the more severe the patient's limitation of movement.

The user computing device further is programmed to communicate the measurement data and any associated score to a health records computing system. For example, the data may be communicated to a service or system that is configured to provide secure storage of the patient's medical records. In an example scenario where the measurements relate to ankylosing spondylitis and a BASMI has been generated, the user computing device may communicate that the patient has taken the BASMI measurements along with the newly generated BASMI score to a physician or health care provider computing system. The physician may access the health record computing system in order to review the measurements and any associated score. If necessary, the physician may follow up with the patient.

It will be appreciated that the disclosed systems and methods allow patients to take clinical measurements such as, for example, the BASMI measurements by themselves and within the comfort of their own home. Accordingly, the disclosed systems remove impediments to taking the clinical measurements more frequently than is currently the practice. As a result, patients receive better care.

BRIEF DESCRIPTION OF THE DRAWINGS

The following description of the illustrative embodiments may be better understood when read in conjunction with the appended drawings. It is understood that potential embodiments of the disclosed systems and methods are not limited to those depicted.

FIG. 3 depicts functional components of an example sensor device.

FIGS. 9A-C depict views of an example sensor device interconnected with an example sensor carrier.

FIGS. 10A-B depict views of an example sensor device and carrier positioned for use by a patient.

FIGS. 16A-E depict views of an example sensor device interconnected with an example sensor carrier.

FIGS. 19A-B depict an example sensor device.

DETAILED DESCRIPTION OF ILLUSTRATIVE EMBODIMENTS

Tracking of physical disease in humans often involves performing physical measurements of a patient's body. For example, tracking of the medical condition known as ankylosing spondylitis involves taking various measurements relating to the patient's flexibility. Development of ankylosing spondylitis is typically tracked using a series of clinical measurements relating to the flexibility of the spine. For example, a series of five defined measurements may be taken and combined to arrive at a score that is evaluated on the Bath Ankylosing Spondylitis Metrology Index (BASMI). The score, which is often referred to as a BASMI score, provides an indication of the severity of a patient's spinal immobility. Other methods or indexes for evaluating progress of ankylosing spondylitis such as the following may likewise involve taking measurements relating to a patient's flexibility: Bath Ankylosing Spondylitis Disease Activity Index; Ankylosing Spondylitis Disease Activity Score; and Bath Ankylosing Spondylitis Global Score.

Disclosed herein are systems comprising sensor devices that may be affixed to a patient and used to perform clinical measurements such as, for example, measurements for evaluating progress of ankylosing spondylitis.

Figure 1:
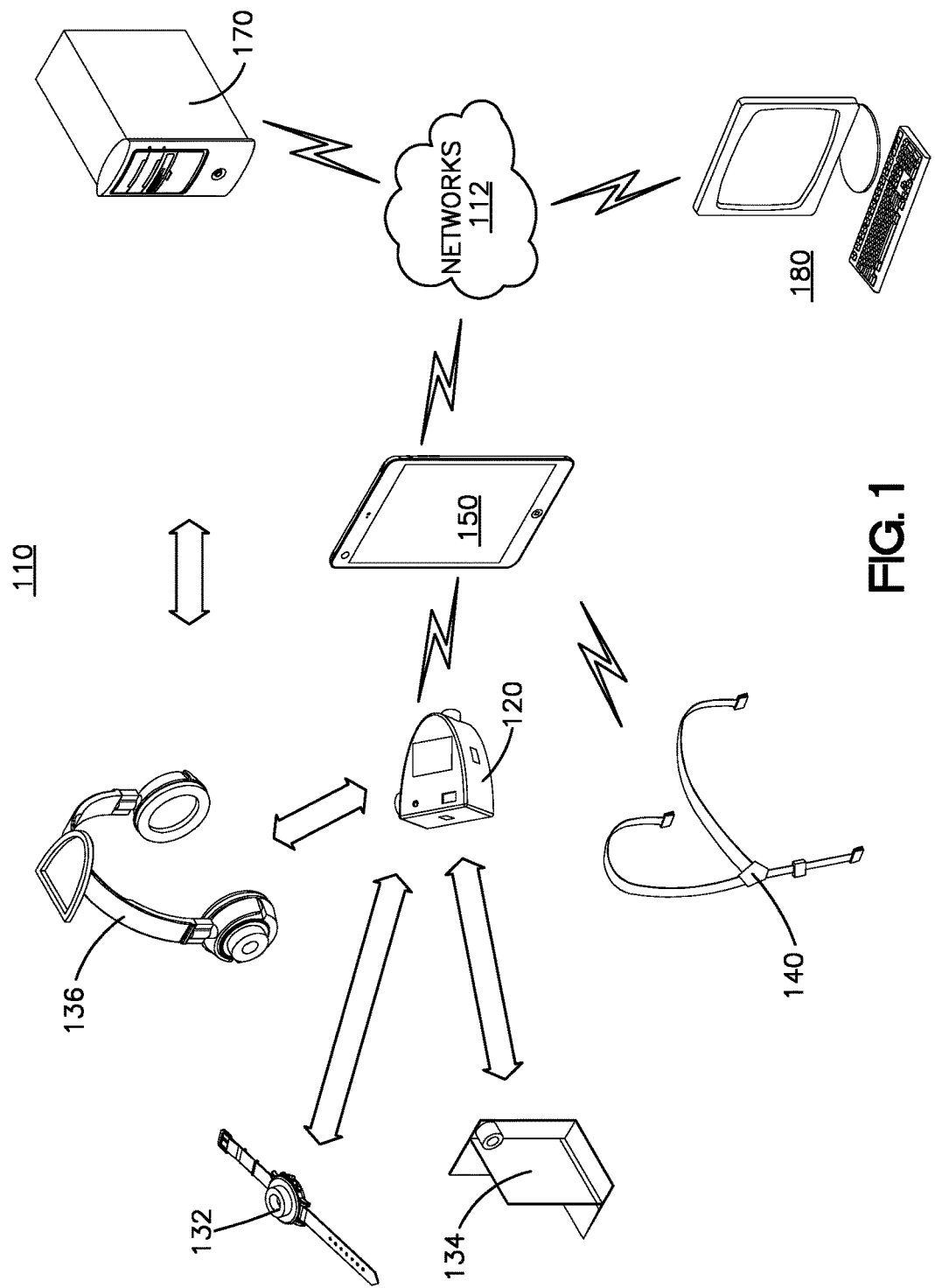
FIG. 1 depicts an example system for taking measurements using sensor devices.

FIG. 1 is a diagram illustrating an example computing environment 110 in which sensor devices 120 and 140 are employed to collect clinical measurements from patients. A first sensor device 120 is successively attached to each of wrist carrier 132, ankle carrier 134, and headset carrier 136. The carriers 132, 134, and 136 are attached to, or positioned next to, the relevant portion of the patient's body in order to perform particular measurements such as, for example, those relating to generating a BASMI index score or similar index score. As the patient performs the routine of motions associated with a particular measurement, the relevant measurements are taken using sensor device 120.

In a first example scenario, sensor device 120 is affixed to wrist carrier 132 for purposes of obtaining lumbar side flexion measurements which may be used, for example, in connection with calculating a BASMI score. Generally, a lumbar side flexion measurement is begun with a patient in a starting position as follows: standing in bare feet; back to wall, knees straight; scapulae, buttocks, and heels against a wall; shoulders level; and outer edges of feet 30 cm apart and parallel. Traditionally, lumbar side flexion measurements involved measuring from the tip of the middle finger to the floor. With palms placed on lateral aspect of thighs, the patient reaches toward the floor by side flexing. The distance from the tip of the middle finger to the floor is re-measured. The difference between the two measurements represents the amount of side flexion. The same measurements are taken for the patient's other hand.

In the context of the disclosed systems, lumbar side flexion measurements are collected by first attaching wrist carrier 132 with sensor device 120 affixed thereto to the patient's arm or hand. For example, wrist carrier 132 may be attached at the patient's wrist. Sensor device 120 and wrist carrier 132 are configured such that when wrist carrier 132 is attached to the patient's arm or hand, a distance sensor within sensor device 120 is positioned to measure the distance between sensor device 120 and the surface on which the patient is standing. The patient uses computing device 150, which may be a smart phone, tablet, or other computing system configured to wirelessly communicate with sensor device 150, to request that sensor device 120 capture the measurements for a lumbar side flexion. As the patient bends sideways in the manner noted above, sensor device 120 measures the change in distance resulting from the patient's side flexion. Sensor device 120 records the measurements and communicates the measurements to user computing device 150.

Sensor device 120 is also configured to be affixed to ankle carrier 134 for purposes of measuring the intermalleolar distance which may be used, for example, in connection with calculating a BASMI score. Traditionally, collecting an intermalleolar distance measurement involves the patient lying supine on the floor or a wide plinth. With knees straight and legs in contact with the resting surface, the patient moves his or her legs as far apart as possible. The distance between the medial malleoli, which generally refers to the area of the ankle, is measured.

In the context of the disclosed systems, intermalleolar distance is measured by first positioning ankle carrier 134 with sensor device 120 affixed thereto adjacent to the patient's ankle. Sensor device 120 and ankle carrier 134 are configured such that when ankle carrier 134 is positioned adjacent to the patient's ankle, a distance sensor within sensor device 120 is positioned to measure the distance between the patient's ankles. Using device 150, the patient requests that sensor device 120 capture measurements of the intermalleolar distance. Thereafter, when the patient spreads his or her legs to the greatest extent possible, sensor device 120 measures the distance between sensor device 120 and the opposing ankle area. Sensor device 120 records the measurements and communicates the measurements to user computing device 150.

Sensor device 120 is also configured to be affixed to headset carrier 136 for purposes of measuring tragus-to-wall distance. Traditionally, a tragus-to-wall distance measurement begins with the patient positioned similarly as at the beginning of the lumbar side flexion measurement. With his or her back to the wall, the patient draws his or her chin in as far as possible. The distance is then measured between the tragus of the ear and the wall.

In the context of the disclosed systems, headset carrier 136 with sensor device 120 affixed thereto is positioned on the patient's head. Headset carrier 136 comprises a harness configured to be positioned on a patient's head. The harness is formed in a generally arcuate shape and comprises at least two connectors configured to be used in affixing sensor device 120 to headset carrier 136 in three different configurations. A first connector is formed proximate an area that, when headset carrier 136 is positioned on the patient's head, the first connector is positioned proximate the patient's ear. When sensor device 120 is affixed to headset carrier 136 using this first connector on headset carrier 136, sensor device 120 is positioned to measure the distance between sensor device 120 and a wall against which the patient stands. Using device 150, the patient requests that sensor device 120 capture measurements of the tragus-to-wall distance. When the patient stands with his or her back to the wall and moves his or her chin inward as far as possible, sensor device 120 measures the distance between the sensor device and the wall. The headset carrier 136 may be re-positioned on the patient's head so that the sensor device 120 is positioned over the patient's second ear. The patient repeats the measurement procedure for the second ear. Sensor device 120 records the measurements and communicates the measurements to user computing device 150.

Sensor device 120 is still further also configured to be affixed to headset carrier 136 for purposes of measuring cervical rotation. Traditionally, cervical rotation measurements begins with the patient supine on a surface with his or her head horizontal and in a neutral position. The patient rotates his or her head as far as possible to one side while keeping his or her shoulders still. A goniometer or inclinometer has typically been used by a health care professional to measure the degree of rotation. The patient then rotates his or head as far as possible to the opposite side while keeping his or her shoulders still, and a health care professional measures the degree of rotation.

In the context of the disclosed systems, sensor device 120 is affixed to a second connector of headset carrier 136 for purposes of measuring cervical rotation. The second connector of headset carrier 136 is formed proximate an area that, when the headset carrier 136 is positioned on the patient's head, the second connector is positioned proximate the crown or top of the patient's head. When sensor device 120 is affixed to headset carrier 136 using this second connector, sensor device 120 is positioned to measure the rotation of the patient's head. Using device 150, the patient requests that sensor device 120 capture measurements of the cervical rotation. This may involve the patient first moving his or her head in a first direction to the greatest extent possible while sensor device 120 measuring the degrees of rotation. The patient then returns his or her head to the initial starting position and rotates his or her head in the opposite direction to the greatest extent possible while sensor device 120 measures the degrees of rotation. Sensor 120 records the measurements and communicates the measurements to device 150.

Referring to FIG. 1, a second sensor device 140 is likewise configured to collect measurements of a patient's movements. In particular, sensor device 140 is configured to collect measurements for lumbar flexion. Traditionally, a patient prepares for measurement of lumbar flexion by standing with the outer edges of his or her feet about 30 cm apart. A health care professional marks a point midway along a line level with the patient's iliac crests. A second point is marked 10 cm above this mark and a third point is marked 5 cm below the first, creating a 15 cm line. The patient flexes forward from the waist with knees fully extended. The distance between the upper and lower two marks is measured. Any increase beyond 15 cm represents the amount of movement achieved.

In the context of the disclosed system, a lumbar flexion measurement may be gathered by first applying sensor device 140 to the patient. Sensor device 140 has a configuration similar to a set of suspenders and, therefore, may be referred to herein as the suspender sensor system. Suspender sensor system 140 comprises a first band configured to be applied over a patient's first shoulder and affixed at one end to a garment proximate the patient's waist, and a second band configured to be applied over the patient's second shoulder and affixed at a first end to a garment proximate the patient's waist. The two bands are coupled at their second ends to a third band. The third band comprises at least a portion that is made of a flexible material that has a sensor attached thereto. An end of the third band is configured to be connected to a garment at the patient's waist. When a patient applies the suspender sensor system to his or her torso, the first two bands are attached to a garment on the front of the patient's torso and the bands extend over the patient's shoulders. The third band extends down the patient's back and is attached at an end to a garment at the patient's waist. Using device 150, the patient request that sensor device 140 capture measurements of the lumbar flexion. When the patient flexes forward from his or her waist, suspender sensor device 140 measures the amount that the flexible portion of the sensor increases in length. Suspender sensor device 140 records the measurements and communicates the measurements to user device 150.

User computing device 150 is programmed to receive the measurement data from sensor devices 120 and 140 and to store the data. Device 150 is further programmed to process the data in order to calculate any relevant scores such as, for example, a BASMI score. For example, for those measurements such as lumbar side flexion, tragus-to-wall, and cervical spine rotation where two separate measurements are taken, one for each side of the body, user device 150 is programmed to calculate a mean of the two measurements. By way of example, user device 150 is programmed to receive two values for tragus-to-wall measurements—one for each ear. Likewise, user device 150 is programmed to receive two values for lumbar side flexion measurements—one for each arm. User device 150 is programmed to receive two values for cervical spine rotation—one for rotation of the head to the left and one for rotation of the head to the right. In connection with each of these instances, user device 150 is programmed to determine a mean value.

User device 150 is further programmed to generate a score value for each of the five measurement types. In an example scenario wherein the score relates to BASMI, the score values for each of the measurement types is generated by comparing the measured values to established intervals that correspond to particular score values ranging from zero to ten as defined by the BASMI index. A value of zero is indicative of little or no disease, a value of ten is a strong indication of disease progression, and values in between zero and ten represent intermediary gradations of disease. User device 150 compares the measured values to the defined intervals to arrive at a score for each of the measurement types.

User device 150 generates a sum by adding the generated score values for each of the five measurements. Finally, in the example scenario wherein the score relates to BASMI, user device 150 generates a composite BASMI score by dividing the generated sum by five. The higher the BASMI score, the more severe the patient's limitation of movement due to ankylosing spondylitis.

User device 150 is programmed to communicate the measurement data and related score to health records computing system 170 via network 112. Health records computing system 170 is programmed to receive a patient's measurements and composite index score and store the data with other data associated with the particular patient. For example, health records computing system 170 is programmed to store the received BASMI data with previous BASMI measurements for the particular patient.

User device 150 is further programmed to communicate a message to physician computing system 180 indicating that the patient has taken the measurements and a new score has been created. Physician system 180 is programmed to allow the physician to access health record computing system 170 via network 112 in order to review the measurements and score. Physician system 180 is further programmed to allow the physician to communicate over network 112 with user device 150.

Network 112 may be any type of network that is suitable for providing communications between system 150, health records system 170, and physician systems 180. Moreover, communications network 112 may comprise a combination of discrete networks which may use different technologies. For example, communications network 112 may comprise local area networks (LANs), wide area networks (WAN's), cellular networks, or combinations thereof. Communications network 112 may comprise wireless, wireline, or combination thereof. In an exemplary embodiment, communications network 112 comprises the Internet and may additionally comprise any networks configured to communicate with the Internet. Still further, the communications network 112 may make use of any suitable protocols such as, for example, Web protocols that employ HTTP.

Figure 2:
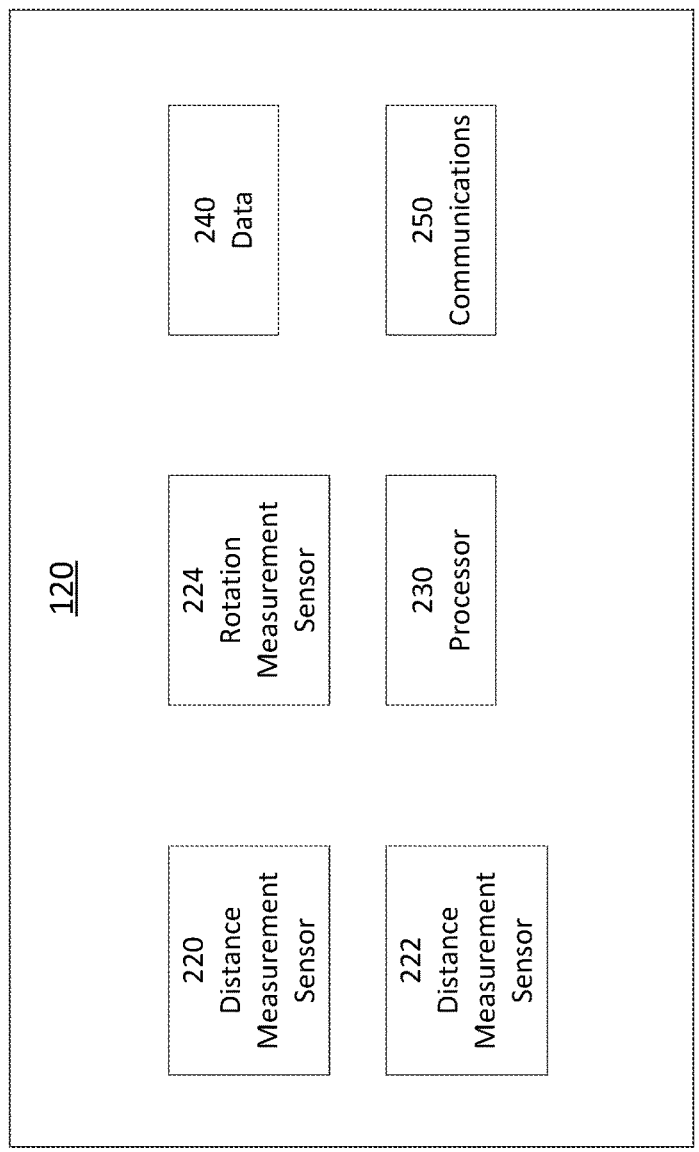
FIG. 2 depicts functional components of an example sensor device.

FIG. 2 depicts a functional block diagram illustrating functional components of an example sensor device 120. As shown, in an example embodiment, sensor device 120 comprises a first distance measurement sensor 220 and a second distance measurement sensor 222. Distance measurement sensors 220 and 222 may be any that are suitable to make distance measurements of the type and distance described herein for analyzing progress of disease including, for example, ankylosing spondylitis. For example, distance measurement sensors 220 and 22 may be any that are suitable for taking lumbar side inflexion measurements, intermalleolar measurements, and tragus-to-wall measurements. In an example embodiment, first distance measurement sensor 220 operates using ultrasonic waves to determine a distance between the sensor and an object. First distance measurement sensor 220 generates ultrasonic waves and receives reflected waves. In an example embodiment, second distance measurement sensor 222 operates using light waves to determine a distance between the sensor and an object. In an example embodiment, second distance measurement sensor transmit light waves and receives the reflected light waves.

In an example embodiment, sensor device 120 comprises a rotation motion measurement sensor 224. Rotation measurement sensor 224 may be any that are suitable to measure the rotation of the sensor device 110 in space. For example, rotation measurement sensor 224 may be any sensor that is suitable for taking cervical rotation measurements as described herein. In an example embodiment, rotation measurement sensor 224 comprises gyroscopic and accelerometer functionality. In an example embodiment, rotation measurement sensor 224 may be a combination of inertial sensors such as, for example, accelerometers, gyro sensors, altimeter sensors, and magneto sensors. For example, rotation measurement sensor 224 may comprise both an accelerometer and magnetometer.

Sensor device 110 comprises a central processor 230 and data storage 240. Central processor 230 is communicatively coupled to each of distance measurement sensors 220 and 222, rotation measurement sensors 224, data storage 240, and communications processor 250. Central processor 230 is programmed to control the operations performed on sensor device 120 including initiating measurements using distance sensors 220 and 222 and rotation measurement sensor 224, receive measurement data from sensors 220, 222, and 224, store measurement data in data storage 240, and control communications processor 230 to initiate communication of measurement data and scores to health care computing system 170.

Sensor device 120 further comprises a communications processor 250 which operates to control communication between sensor device 120 and user computing system 150. For example, communications processor 250 may provide communication via any suitable protocol such as, for example, Bluetooth.

FIG. 3 depicts a functional block diagram illustrating functional components of an example suspender sensor 140. As shown, in an example embodiment, suspender sensor 140 comprises a stretch measurement sensor 320. Stretch measurement sensor 320 may be any that is suitable to make measurements of the type and distance described herein for lumbar flexion. In an example embodiment, stretch sensor functionality 320 operates to measure the length by which a flexible band increases in length over time. Suspender sensor 140 further comprises central processor 330, data storage 340, and communications processor 350 which provide processing analogous to that described above in connection blocks 230, 240, and 250 of FIG. 2.

Sensor Device and Wrist Carrier

Figure 4A:
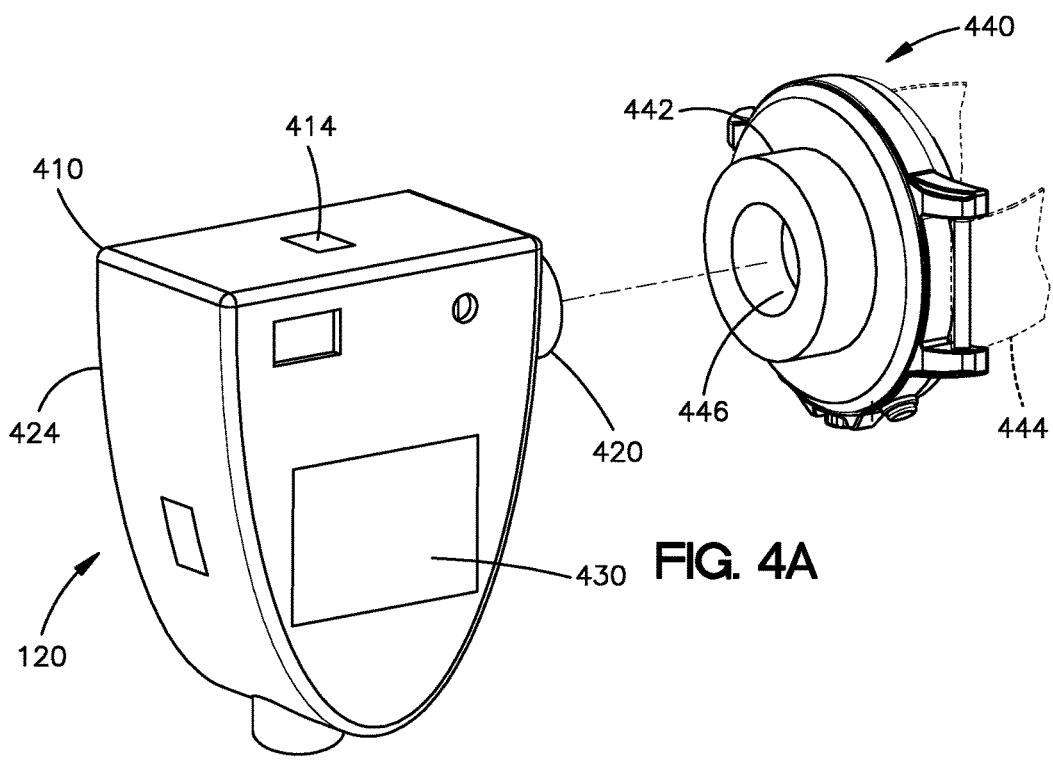
FIGS. 4A-B depict perspective views of an example sensor device aligned for interconnection with an example sensor carrier.
Figure 4B:
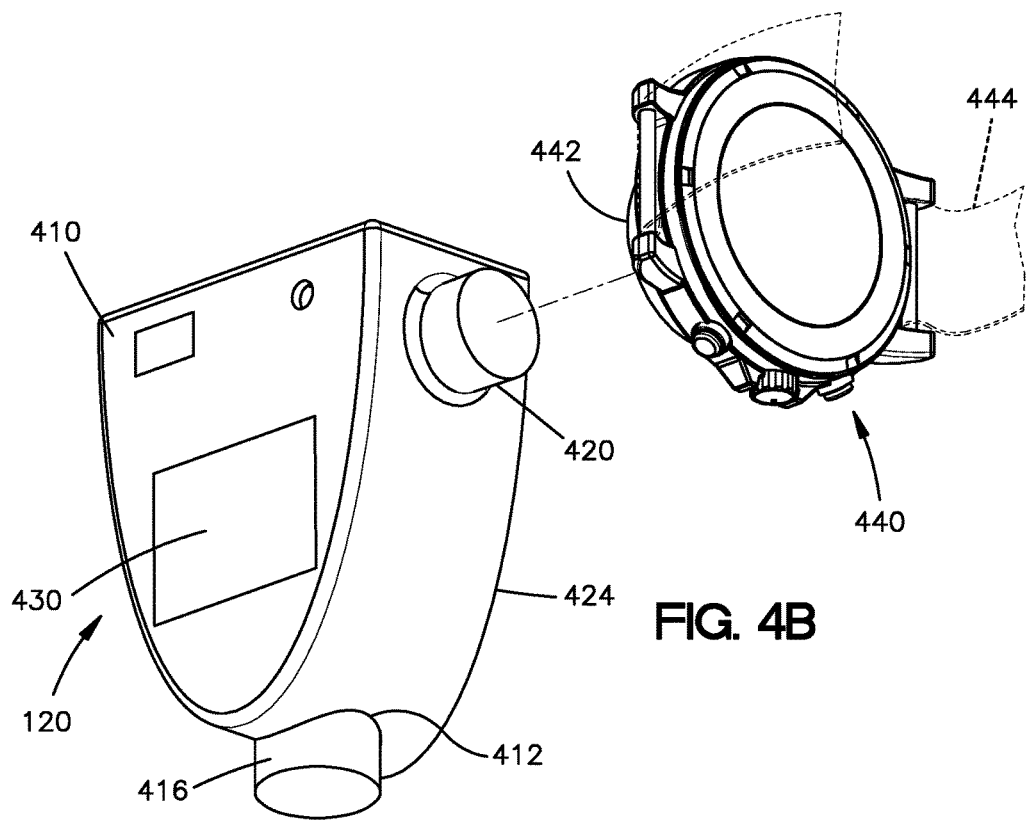

FIGS. 4A and 4B depict views of an example first sensor device 120 aligned to be attached with wrist carrier 132. As shown, sensor device 120 comprises casing 410 which houses various computing components including a first distance detector, a second distance detector, and a rotational detector. In the example embodiment disclosed in FIGS. 4A and 4B, casing 410 has apertures 412 and 414 formed therein. In an example embodiment, apertures 412 and 414 are formed to coincide with distance measurement sensors comprised in casing 410. Apertures 412 and 414 each provide an opening through which a distance sensor may transmit signals and receive signals in connection with determining a distance. For example, where a first distance measurement sensor comprised in casing 410 uses sound waves to determine the distance between sensor device 120 and an object, an aperture 412 in casing 410 is sufficiently large to allow a portion 416 of the distance sensor to extend through the casing so as to send and receive signals such as ultrasonic signals. A second aperture 414 in casing 410 is sufficient large to allow a second distance measurement sensor within sensor device 120 to send and receive light waves. More particularly, second aperture 414 may be sufficiently large to transmit light waves from the second distance measurement sensor and receive reflected light at the second sensor. In the example embodiment depicted in FIGS. 4A and 4B, first aperture 412 and a corresponding distance sensor are formed at a first end of sensor device 120, and second aperture 414 and second distance sensor are formed at a second end. The first end 410a can be spaced opposite the second end 410b such that the first distance measurement sensor is configured so as to send and receive ultrasonic signals along a first direction and the second distance measurement sensor is configured so as to send and receive light waves in a second direction, opposite the first direction. Alternatively, the first end 410a can be angularly offset from (i.e., non-parallel to) the second end 410b such that the first distance measurement sensor is configured so as to send and receive ultrasonic signals along a first direction and the second distance measurement sensor is configured so as to send and receive light waves in a second direction that is angularly offset from the first direction.

Sensor device 120 comprises connectors that are formed thereon to allow sensor device 120 to be affixed or attached to carriers 132, 134, and 136. In an example embodiment as depicted in FIGS. 4A-B, a first connector 420 comprises a male portion that extends from casing 420 and is shaped to be received into a corresponding female connector comprising a recess. In an example scenario, first connector 420 has a substantially circular cross section.

A second connector 424 is formed by an edge of casing 410. Edge 424 is shaped to correspond to a receiving recess in headset carrier 136 as described below in connection with FIGS. 12A-B.

It will be appreciated that in the example embodiment disclosed in FIGS. 4A-B, connectors 420 and 424 may have any shape and configuration suitable to connect sensor device 120 to carriers 132, 134, and 136. For example, connectors 420 may have a non-circular cross section. Connector 424 may comprise an edge that forms a shape different than that depicted. In still further embodiments, connectors 420 and 424 may be Velcro fasteners.

Sensor device 120 comprises user interface features such as a visual display 430. In an example embodiment, sensor device 120 displays on visual display 430 information regarding the operating conditions of sensor device 120. For example, sensor device 120 may display on visual display 430 information indicating whether or not device 120 is powered on, whether or not device 120 is taking measurements, and/or whether or not device 120 is communicating data to user computing system 150.

FIGS. 4A and 4B also depict an example embodiment of wrist carrier 440. As shown, in an example embodiment, wrist carrier 440 comprises a connector 442 and a strap 444 (shown in dotted lines for clarity). Strap 444 is secured or connected to connector 442 and is used to attach wrist carrier 440 to a patient's arm or hand. Strap 444 may be any that is suitable to removably attach carrier 440 to the patient. Accordingly, strap 444 is sufficiently long to wrap around a patient's arm or hand. In an example embodiment, strap 444 may have a Velcro portion that allows strap 444 to be easily applied and removed. In another embodiment, strap 444 may comprise a buckle that allows strap 444 to be applied and removed to a patient.

Wrist carrier connector 442 may be any that is suitable to interconnect sensor device 120 with wrist carrier 440 in a manner to allow sensor device 120 to obtain measurements as described herein. In an example embodiment, wrist carrier connector 442 is a female connector comprising a recess 446 for receiving a male connector portion on sensor device 410. In an alternative embodiment, wrist carrier connector 442 may be a Velcro fastener positioned to receive a corresponding Velcro fastener on sensor device 120.

Figure 5A:
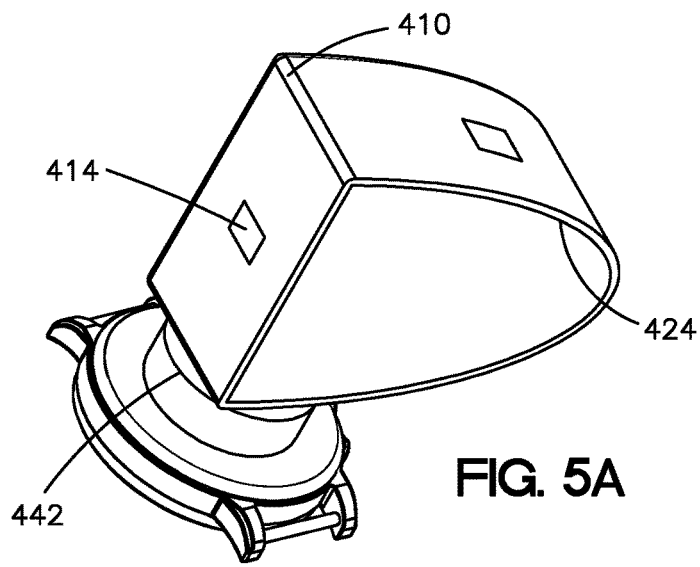
FIGS. 5A-C depict views of an example sensor device interconnected with an example sensor carrier.
Figure 5B:
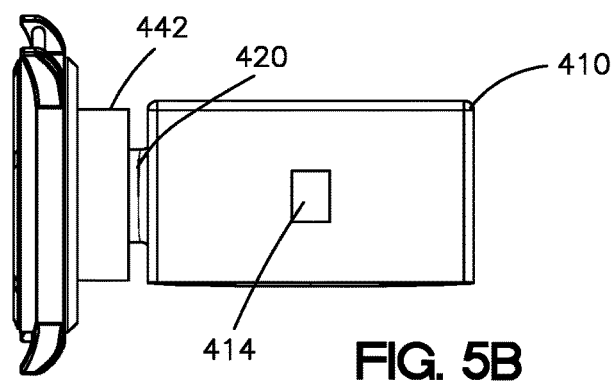
Figure 5C:
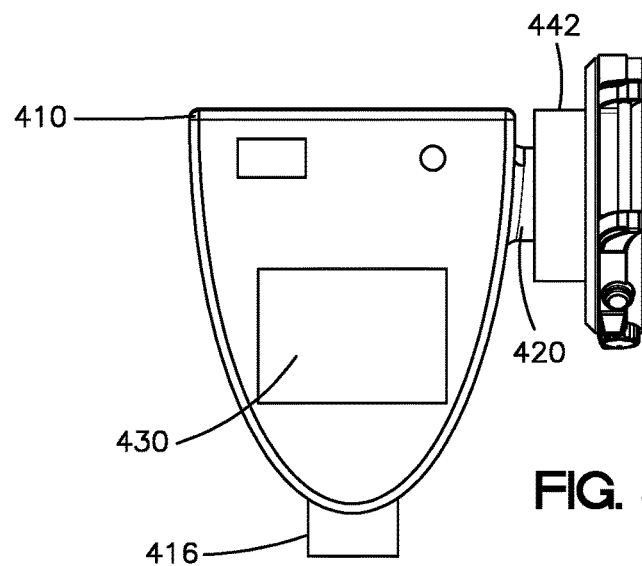

In the scenario depicted in FIGS. 4A and 4B, first connector 420, which is a male connector, is aligned to be received into recess 446 created by wrist carrier connector 442. FIGS. 5A, 5B, and 5C illustrate various views of sensor device 120 attached to wrist carrier connector 442. As shown, first connector 420 of sensor device 120 has been received into connector 442. When the sensor device 120 is attached or joined with wrist carrier 132, the combined unit may be attached to a patient for purposes of gathering measurements.

Figure 6A:
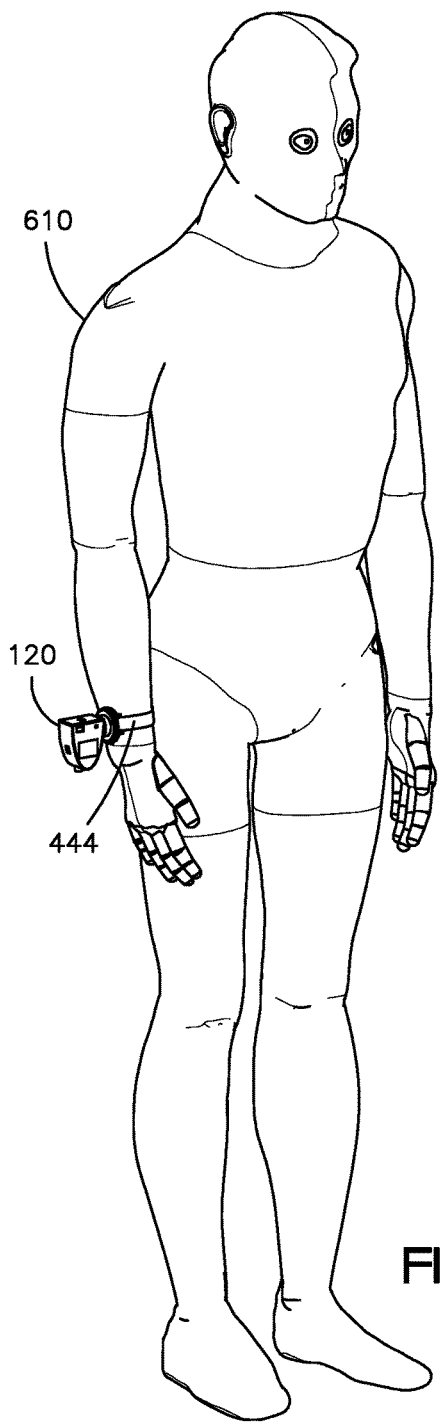
FIGS. 6A-B depict views of an example sensor device and carrier attached to a patient.
Figure 6B:
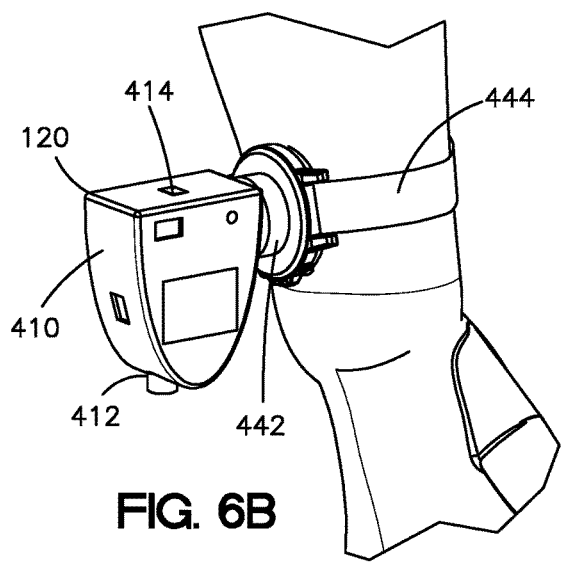

FIGS. 6A and 6B illustrate the interconnected wrist carrier 132 and sensor device 120 attached to a patient 610. As shown, wrist carrier 132 has been attached to patient 610 using strap 444. It will be appreciated that in the demonstrated scenario where wrist carrier 132 has been applied to a patient, a distance measurement sensor within sensor device 120 is positioned to measure the distance between the sensor and the surface on which the patient is standing. In other words, the sensor is positioned to take distance readings downwards to the floor. In an example embodiment, aperture 412 in casing 410 is positioned toward the surface on which the patient is standing. In an example embodiment, a portion 416 of a distance measurement sensor may extend from aperture 412 to facilitate collecting measurement data.

It will be appreciated that while wrist carrier 132 is depicted as being attached to patient 610 in the area of the patient's wrist, wrist carrier 132 may be applied at any suitable location of the patient's arm or hand that allows for a change in distance between the sensor and the floor to be measured when the patient performs the motion associated with a lumbar side flexion measurement.

Figure 7:
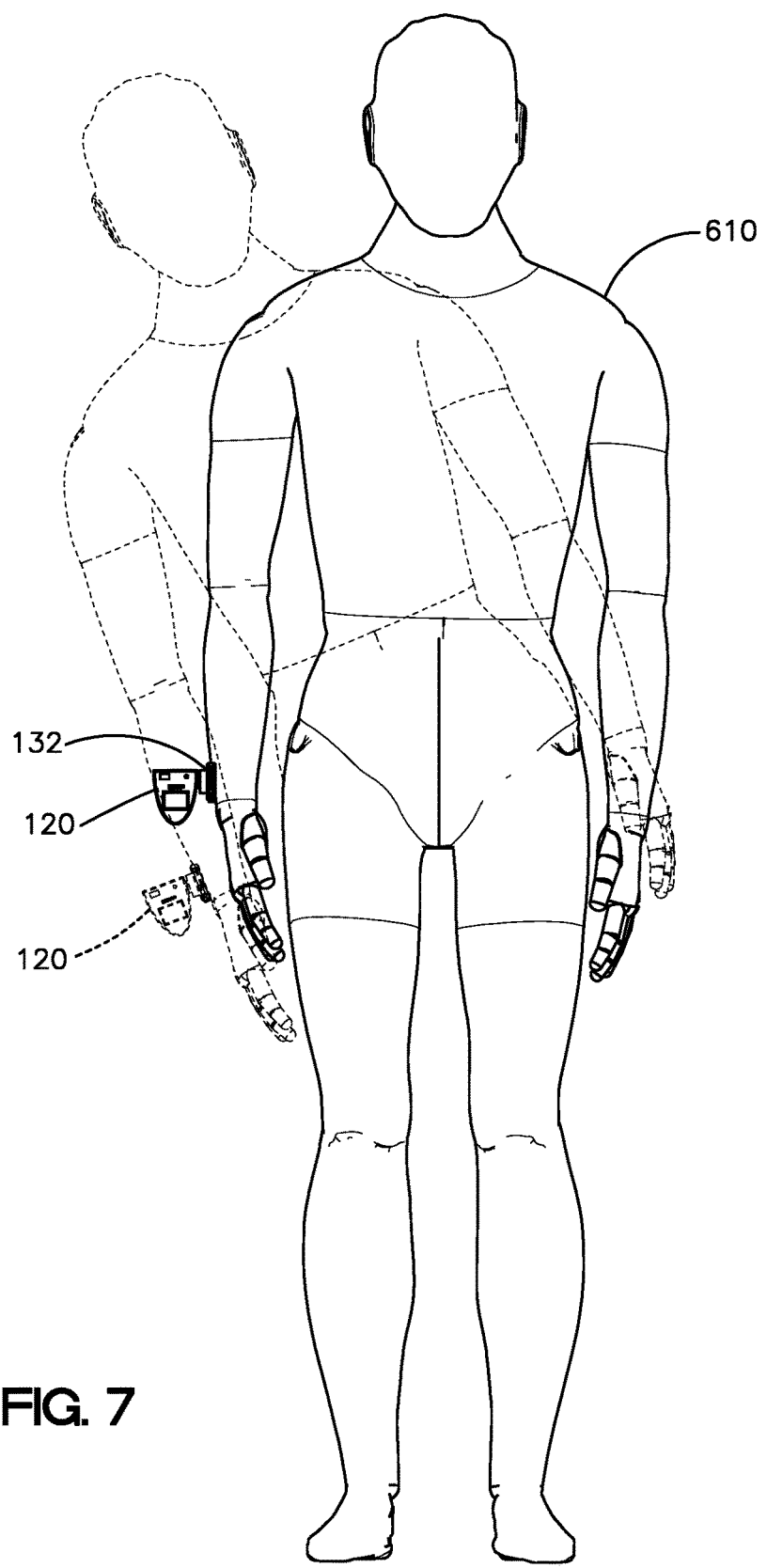
FIG. 7 depicts a view of a patient performing a movement for measurement by an example sensor device.

FIG. 7 illustrates a patient 610 with wrist carrier 132 and sensor device 120 attached bending to the side as part of a lumbar side flexion measurement process. As illustrated by the solid lines, patient 610 begins by standing with arms at his or her side and with feet parallel and about 30 cm apart at the exterior. Sensor device 120 is programmed to take a distance reading in this initial position between the sensor and the floor below patient 610. The patient then bends to the side to the greatest extent possible while keeping his or her legs straight. Sensor device 120 is programmed to detect the distance between device 120 and the floor when the device 120 reaches its closest position to the floor. Sensor device 120 is programmed to calculate the difference in distance between the starting distance and the distance closest to the floor. The patient repeats the process with wrist carrier 132 and sensor device 120 applied to his or her second hand. Sensor device 120 is programmed to communicate the two difference measurements to user system 150 where the measurement data is processed as described below.

Sensor Device and Ankle Carrier

Figure 8B:
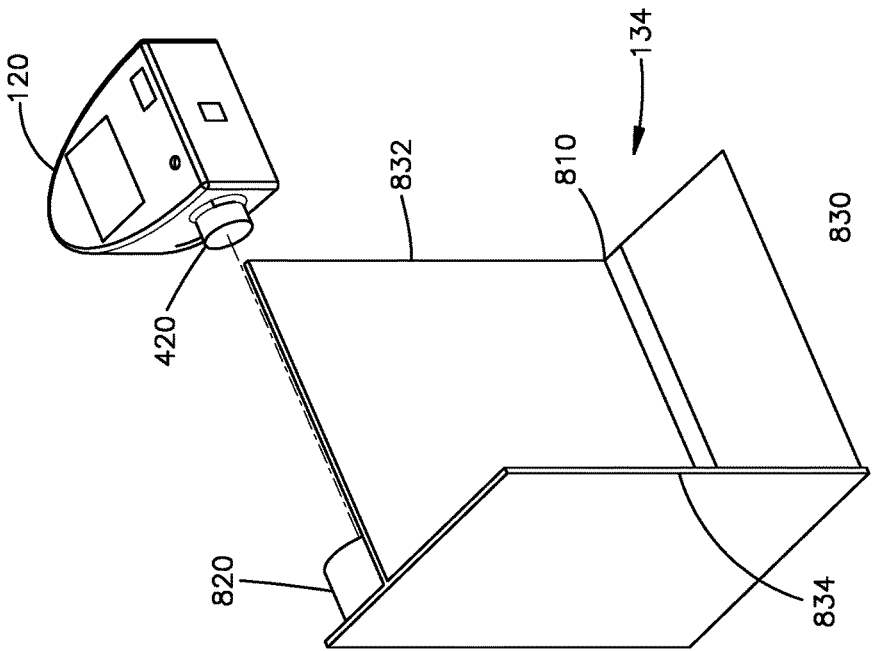
FIGS. 8A-B depict perspective views of an example sensor device aligned for interconnection with an example sensor carrier.
Figure 8A:
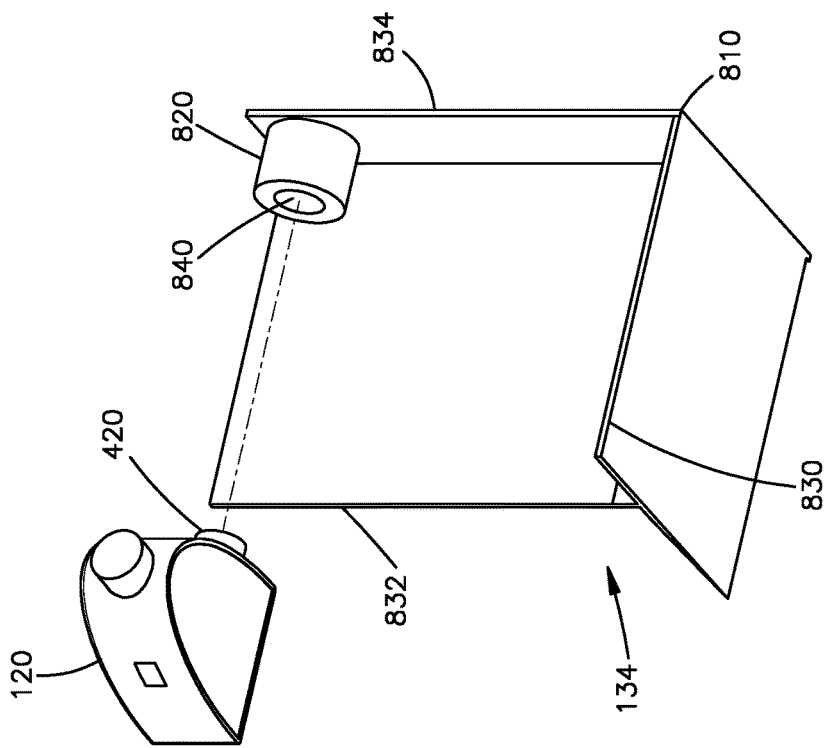

FIGS. 8A and 8B depict sensor device 120 aligned for interconnection with ankle carrier 134. Ankle carrier 134 comprises a frame 810 with connector 820 formed thereon. In an example embodiment, frame 810 comprises a first portion 830 which may be referred to as a bottom portion. Bottom portion 830 is a planar wall configured to abut a portion of a patient's foot when carrier 134 is positioned for taking measurements. Frame 810 further comprises a second portion 832 that extends, at least in part, in a substantially upward direction away from the bottom portion 830. In an example embodiment, upwardly extending portion 832 is a planar wall that extends substantially perpendicularly relative to bottom portion 830. Upwardly extending portion 832 is configured to abut a patient's ankle when carrier 134 is positioned to take measurements. Frame 810 further comprises a third portion 834 that is a planar wall which extends, at least in part, substantially perpendicular to the bottom portion 830 and the upwardly extending portion 832. As shown, in an example embodiment, upwardly extending portion 832 intersects with bottom portion 830 and third portion 834 forming a first area for abutting a patient's foot and ankle and a second portion for receiving sensor device 120.

Connector 820 may be any connector type that is suitable to interconnect sensor device 120 with ankle carrier 134 in a manner to allow sensor device 120 to obtain measurements as described herein. In an example embodiment, connector 820 is a female connector comprising a recess 840 configured to receive a male connector 420 on sensor device 120. In an alternative embodiment, connector 820 may be a Velcro connector configured to receive connector 420 which is also a Velcro connector.

In the scenario depicted in FIGS. 8A and 8B, first connector 420, which is a male connector, is aligned to be received into recess 840 created by connector 820. FIGS. 9A, 9B, and 9C illustrate various views of sensor device 120 attached to connector 820 and ankle carrier 134. As shown, first connector 420 of sensor device 120 has been received into connector 820. When the sensor device 120 is attached or joined with ankle carrier 134, the combined unit may be attached to a patient for purposes of gathering measurements.

FIGS. 10A and 10B illustrate ankle carrier 134 with sensor device 120 affixed thereto positioned for use by patient 610. As shown, ankle carrier 134 has been positioned under the foot of patient 610. The bottom of the patient's foot abuts bottom portion 830 while the inner ankle of the patient abuts uprising portion 832. The heel of the patient's foot abuts third portion 834. It will be appreciated that in the demonstrated scenario where ankle carrier 134 has been applied to a patient, a distance measurement sensor within sensor device 120 is positioned to measure the distance between the sensor and the ankle area of the patient's opposing leg. In other words, the sensor is positioned to take distance readings sideways away from the inner part of the patient's ankle toward the patient's opposite ankle. In an example embodiment, aperture 412 in casing 410 is positioned toward the ankle opposing the foot to which ankle carrier 134 is applied. In an example embodiment, a portion 416 of a distance measurement sensor may extend from aperture 412 to facilitate collecting measurement data.

Figure 11:
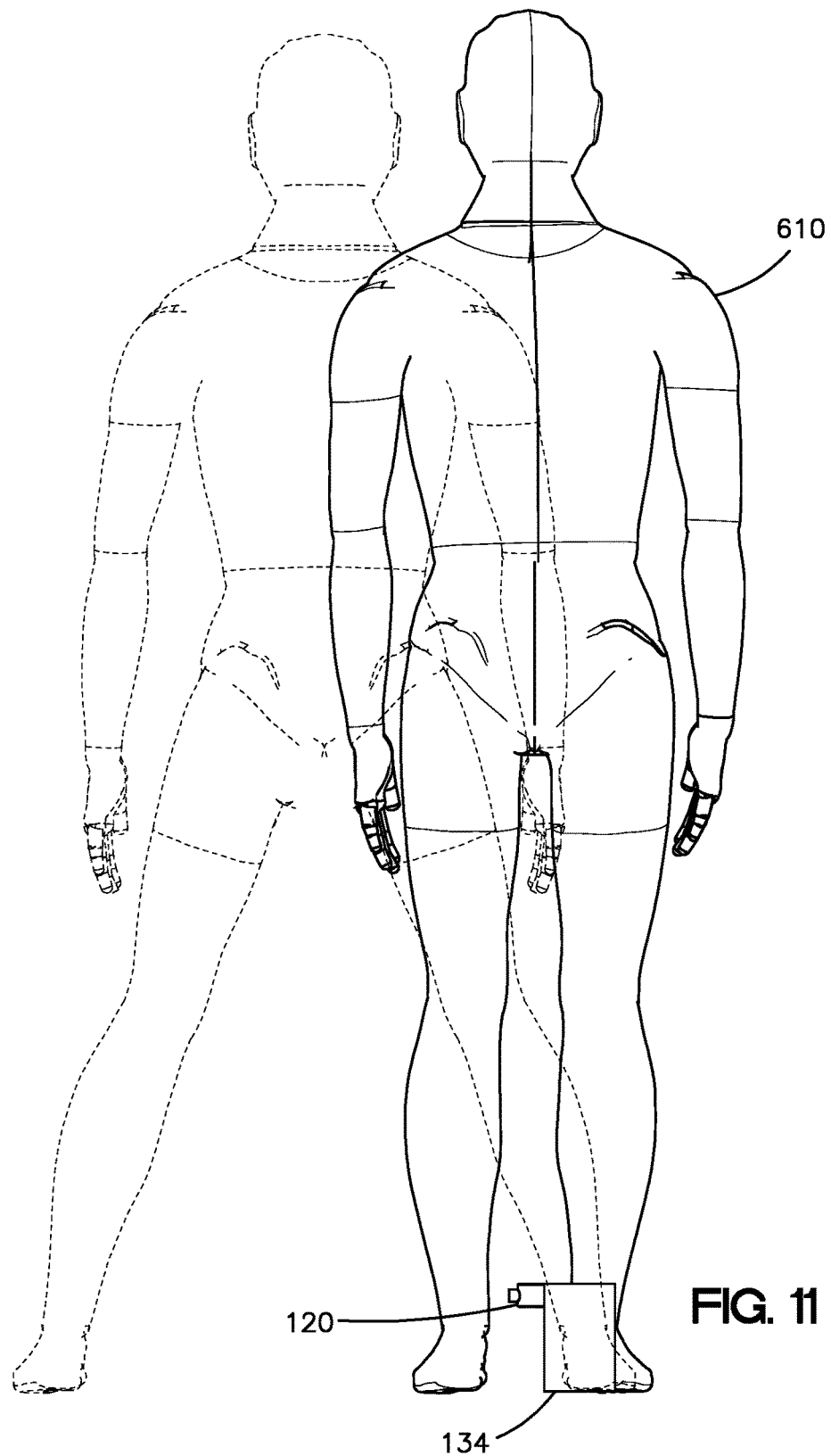
FIG. 11 depicts a view of a patient performing a movement for measurement by an example sensor device.

FIG. 11 illustrates a patient 610 with ankle carrier 134 and sensor device 120 positioned proximate the patient's foot and ankle in preparation for measuring intermalleolar distance. In an example scenario, patient 610 begins the processing lying on his or her back with knees extended. The patient then takes his or her legs as far apart as possible while maintaining the legs in full extension. Sensor device 120 is programmed to detect the distance between device 120 and the ankle area of the opposing leg. The maximum distance between the device and the opposing ankle is recorded. Sensor device 120 is programmed to communicate the maximum distance to user system 150 where the measurement data is processed as described below.

Sensor Device and Headset Carrier

Figure 12A:
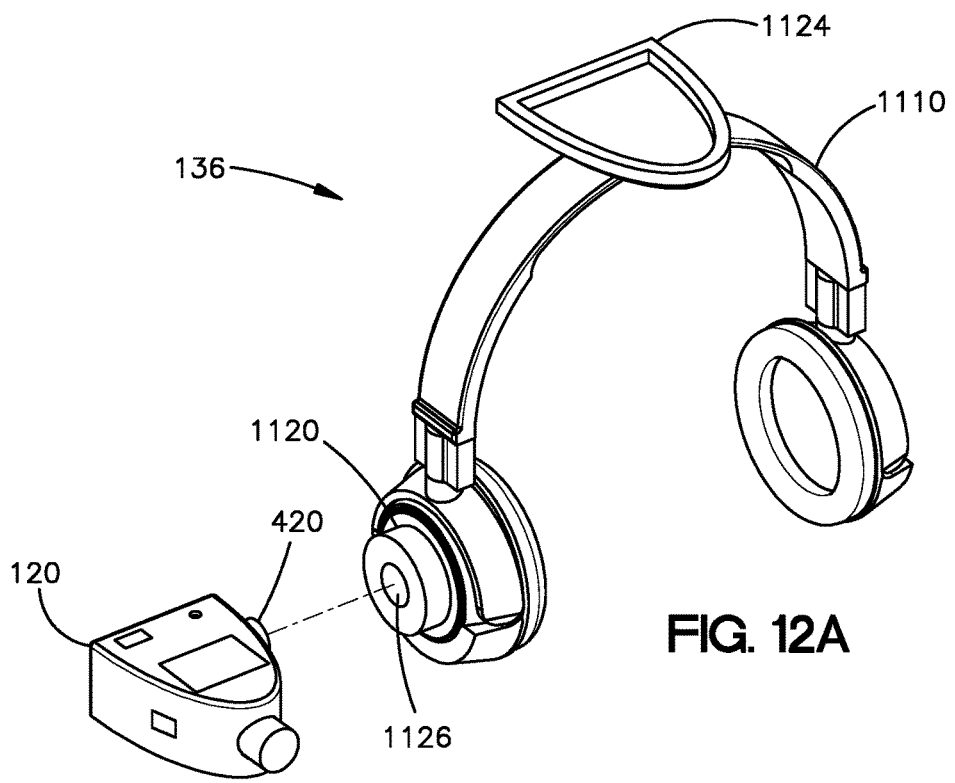
FIGS. 12A-B depict perspective views of an example sensor device aligned for interconnection with an example sensor carrier.
Figure 12B:
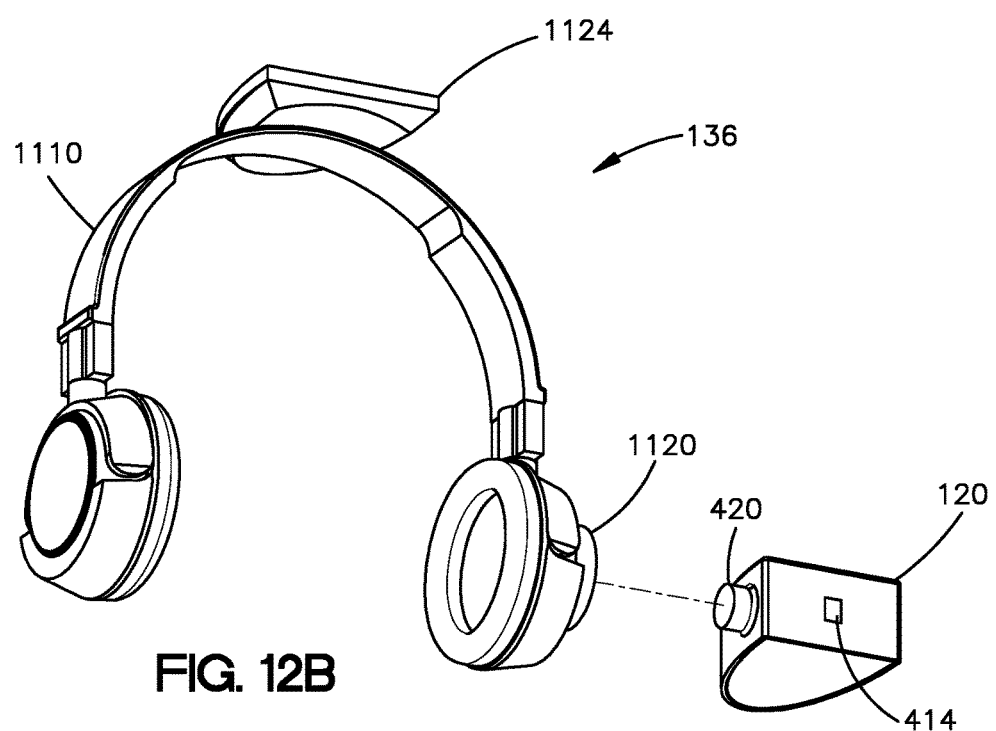
Figure 13B:
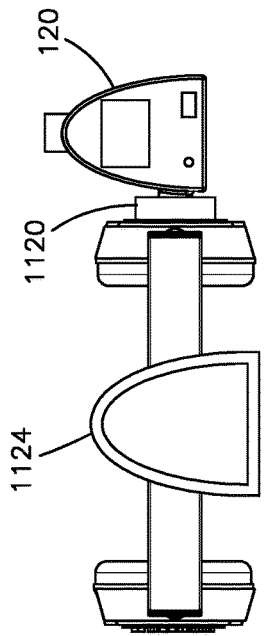
FIGS. 13A-D depict views of an example sensor device interconnected with an example sensor carrier.
Figure 13A:
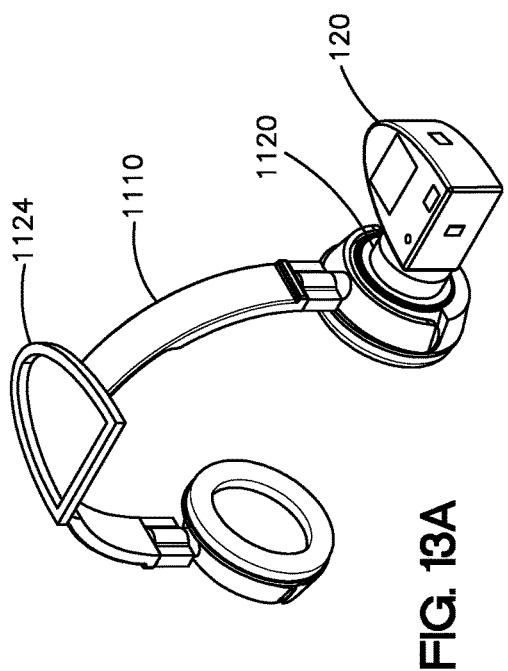
Figure 13D:
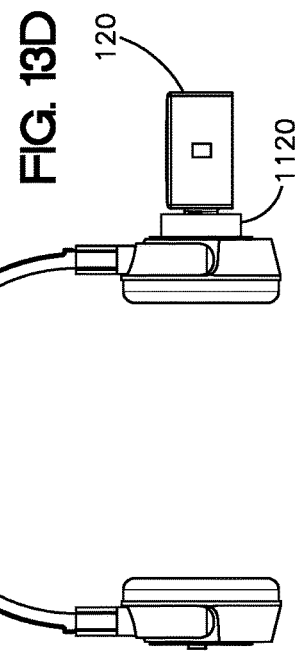
Figure 13C:
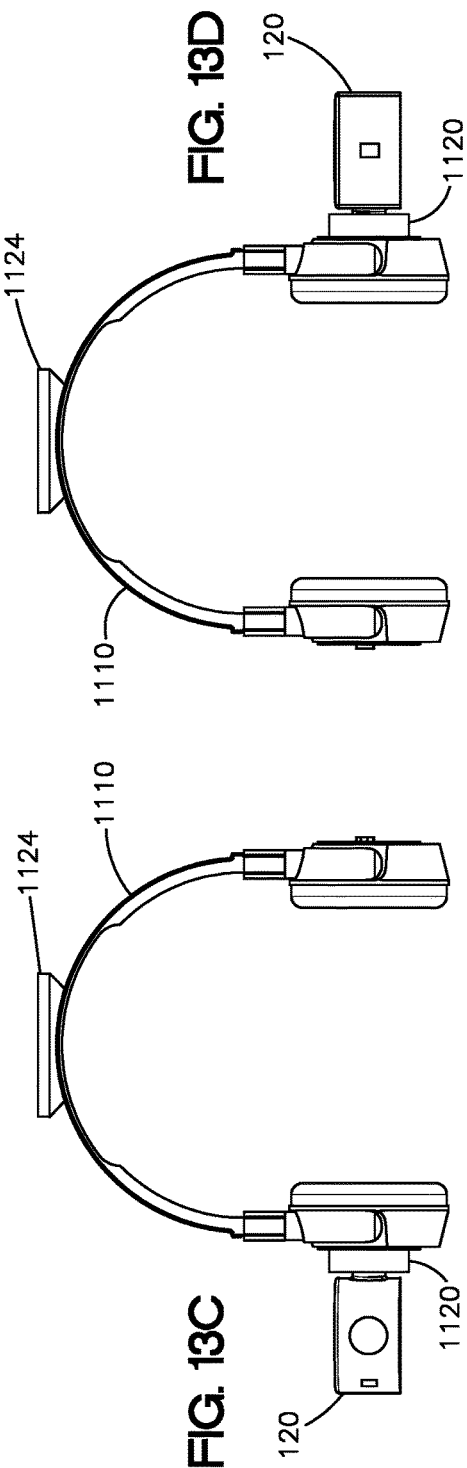

FIGS. 12A and 12B depict sensor device 120 aligned for interconnection with a first connector of headset carrier 136. As shown, in an example embodiment, headset carrier 136 comprises a harness 1110 that is formed in a generally arcuate shape such that harness 1110 may be positioned on a patient's head. Headset carrier 136 further comprises at least a first connector 1120 and a second connector 1124. First connector 1120, which may be referred to as the tragus connector, is attached near a terminus of harness 1110 such that when harness 1110 is positioned on a patient's head, first connector 1120 is generally aligned with the patient's ear. Second connector 1124, which may be referred to as the rotation connector, is connected to harness 1110 at or near the apex of the arcuate shape formed by harness 1110.

In the example scenario depicted in FIGS. 12A and 12B, sensor device 120 is aligned for interconnection with tragus connector 1120. Tragus connector 1120 may be any connector that is suitable to interconnect sensor device 120 with headset carrier 136 in a manner to allow sensor device 120 to obtain tragus-to-wall measurements as described herein. In an example embodiment, tragus connector 1120 is a female connector comprising a recess 1126 for receiving a male connector portion 420 on sensor device 120. In an alternative embodiment, tragus connector 1120 may be a Velcro connector configured to receive a Velcro fastener on sensor device 120.

In the scenario depicted in FIGS. 12A and 12B, first connector 420, which is a male connector, is aligned to be received into recess 1126 created by tragus connector 1120. FIGS. 13A-D illustrate various views of sensor device 120 attached to tragus connector 1120. As shown, connector 420 of sensor device 120 has been received into tragus connector 1120. When the sensor device 120 is attached or joined with headset carrier 136, the combined unit may be positioned on a patient for purposes of gathering tragus-to-wall measurements.

Figures 14A, 14B:
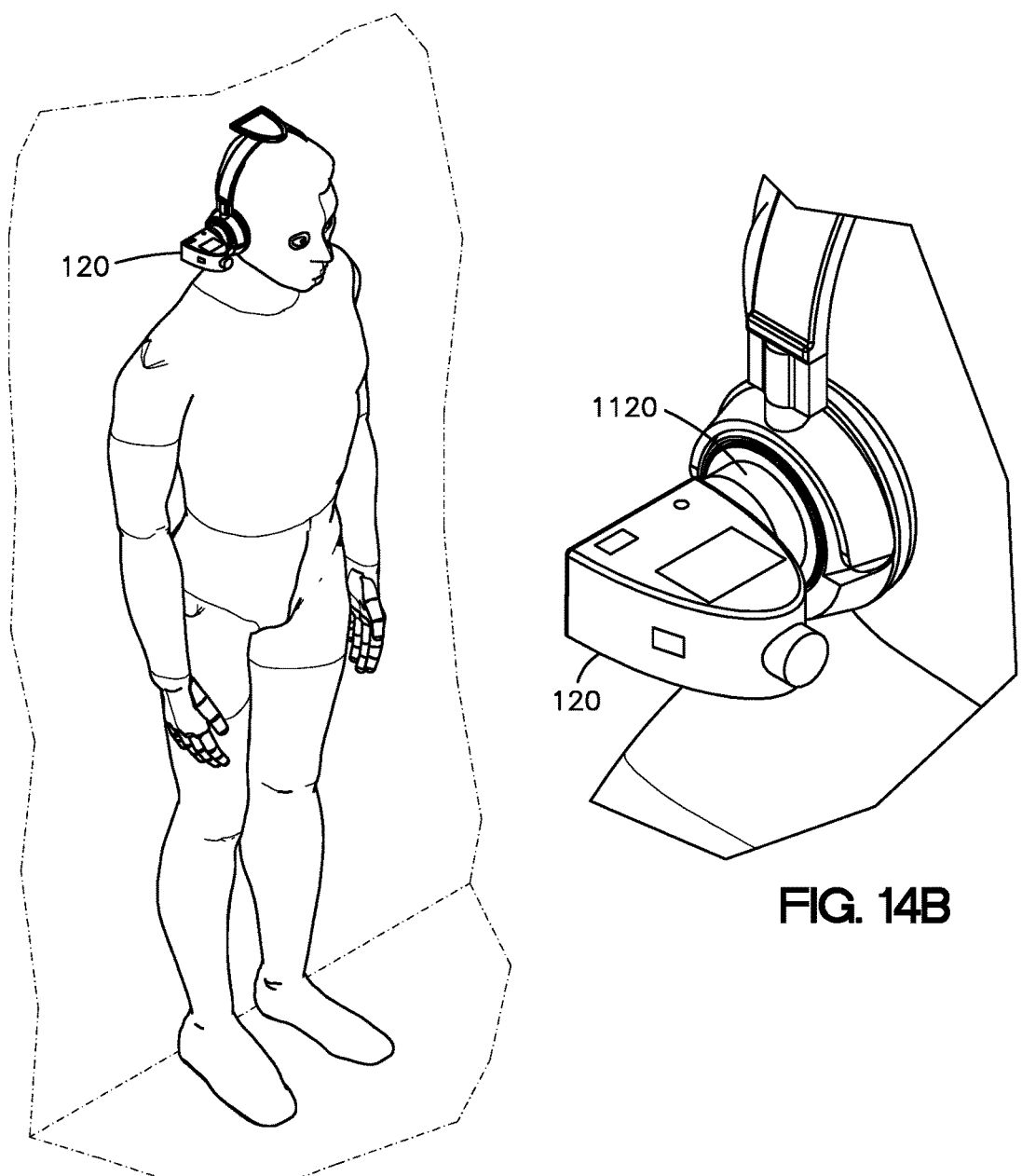
FIGS. 14A-C depict views of an example sensor device and carrier positioned for use by a patient.
Figure 14C:

FIGS. 14A-C illustrate headset carrier 136 with sensor device 120 affixed thereto positioned on patient 610. As shown, headset carrier 136 has been positioned on the patient's head so that the arcuate shape of harness 1110 aligns with the crown of the patient's head. It will be appreciated that in the demonstrated scenario where sensor device 120 has been connected to tragus connector 1120 and headset carrier 136 has been positioned on the patient's head, a distance measurement sensor within sensor device 120 is positioned to measure the distance between the sensor and a surface against which the patient is standing. In other words, the sensor is positioned to take distance readings toward the wall against which the patient is standing. In an example embodiment, aperture 414 in casing 410 is positioned toward the wall against which the patient is standing. In an example scenario, a distance sensor within sensor device 120 transmits light through aperture 414 and uses reflected light received at aperture to measure distance between device 120 and the wall. Once the tragus-to-wall distance has been measured for a patient's first ear, the headset carrier 136 may be repositioned on the patient's head so that connector 1120 and device 120 are positioned over the patient's second ear. In some embodiments, sensor device 120 may be reattached to connector 1120 so that the distance sensor and aperture 414 are positioned toward the wall for the new configuration. The distance between the sensor and wall is then measured and stored. Sensor device 120 is programmed to transmit the measurement data to user system 150 where the data is processed as described below.

Figure 15:
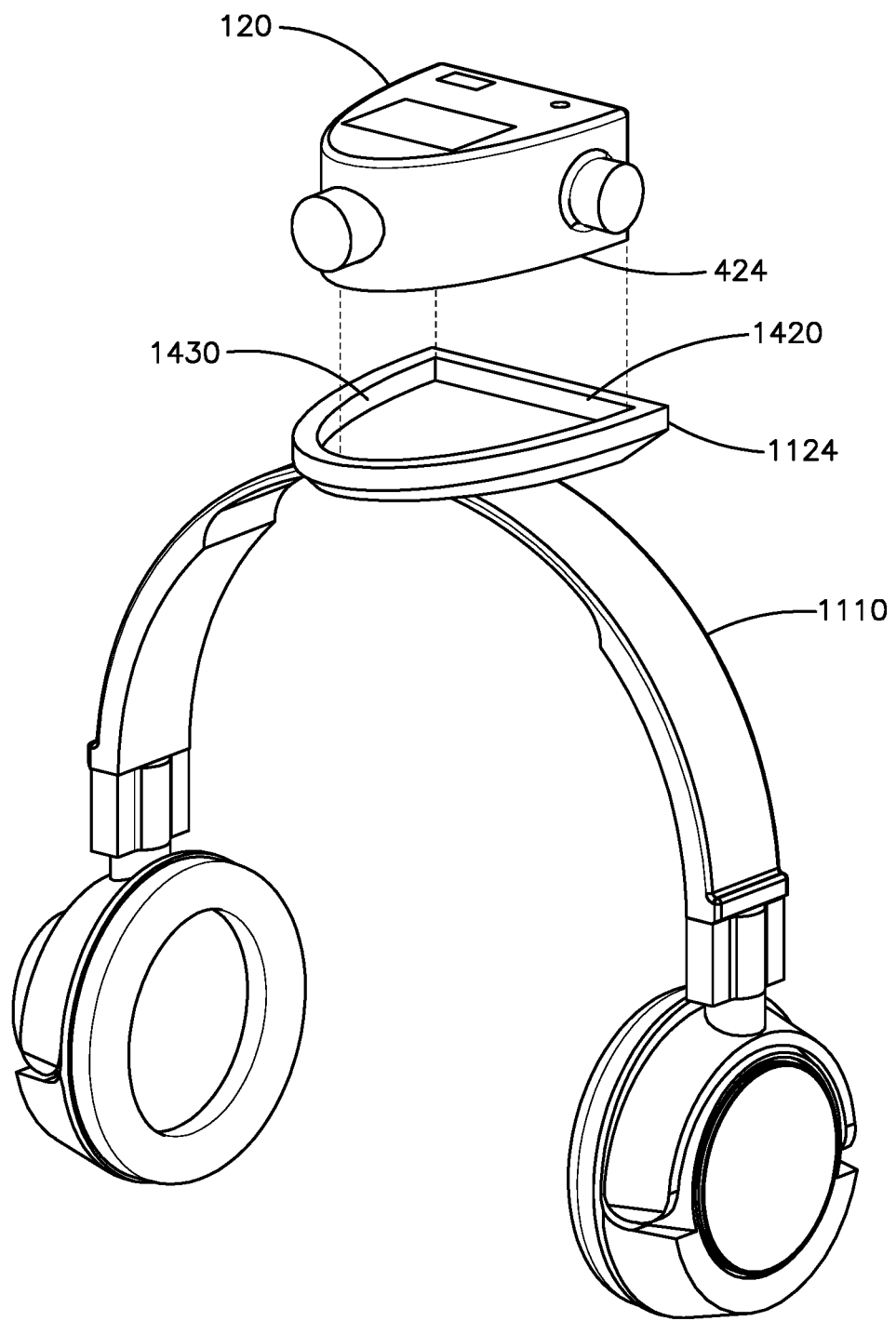
FIG. 15 depicts a perspective view of an example sensor device aligned for interconnection with an example sensor carrier.

FIG. 15 depicts sensor device 120 aligned for interconnection with the second connector, referred to as rotation connector 1124, of headset carrier 136. As shown, rotation connector 1124 is connected to harness 1110 at or near the apex of the arcuate shape formed by harness 1110. Rotation connector 1124 may be any connector that is suitable to interconnect sensor device 120 with headset carrier 136 in a manner to allow sensor device 120 to obtain cervical rotation measurements as described herein. In an example embodiment, rotation connector 1124 is a female connector comprising a recess 1420 for receiving a corresponding connector portion 424 on sensor device 120. More particularly, in an example embodiment rotation connector 1124 comprises rim 1430 that forms an interference fit with edge 424 of sensor device 424. In an alternative embodiment, rotation connector 1124 may be a Velcro fastener configured to interface with a Velcro fastener on sensor device 120.

FIGS. 16A-E illustrate various views of sensor device 120 attached to rotation connector 1124. As shown, connector 424 of sensor device 120 has been received into rotation connector 1124. When the sensor device 120 is attached or joined with headset carrier 136, the combined unit may be positioned on a patient for purposes of gathering cervical rotation measurements.

Figure 17A:
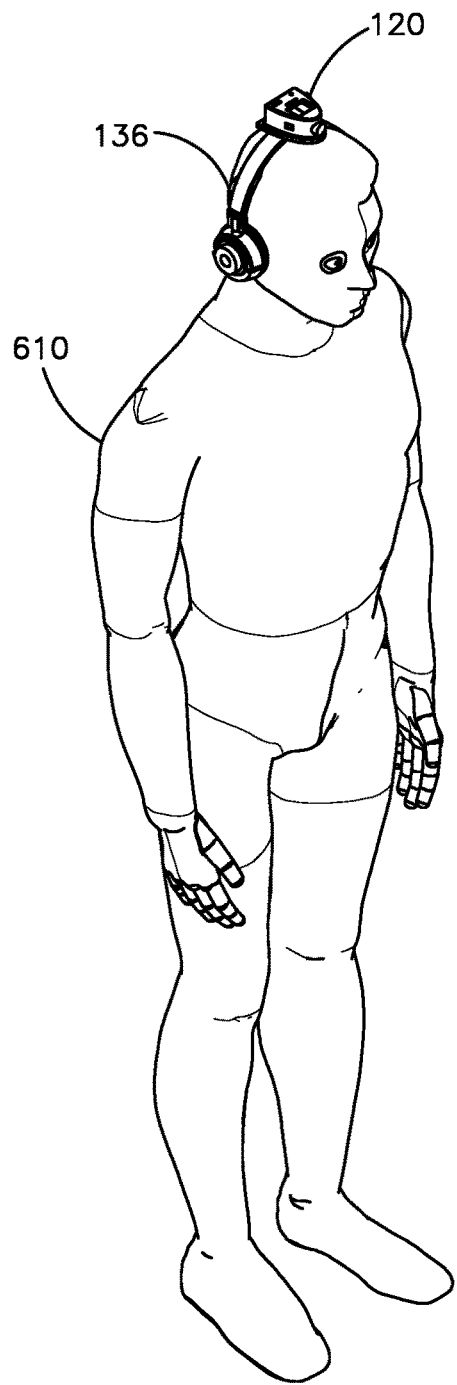
FIGS. 17A-B depict views of an example sensor device and carrier positioned for use by a patient.
Figure 17B:
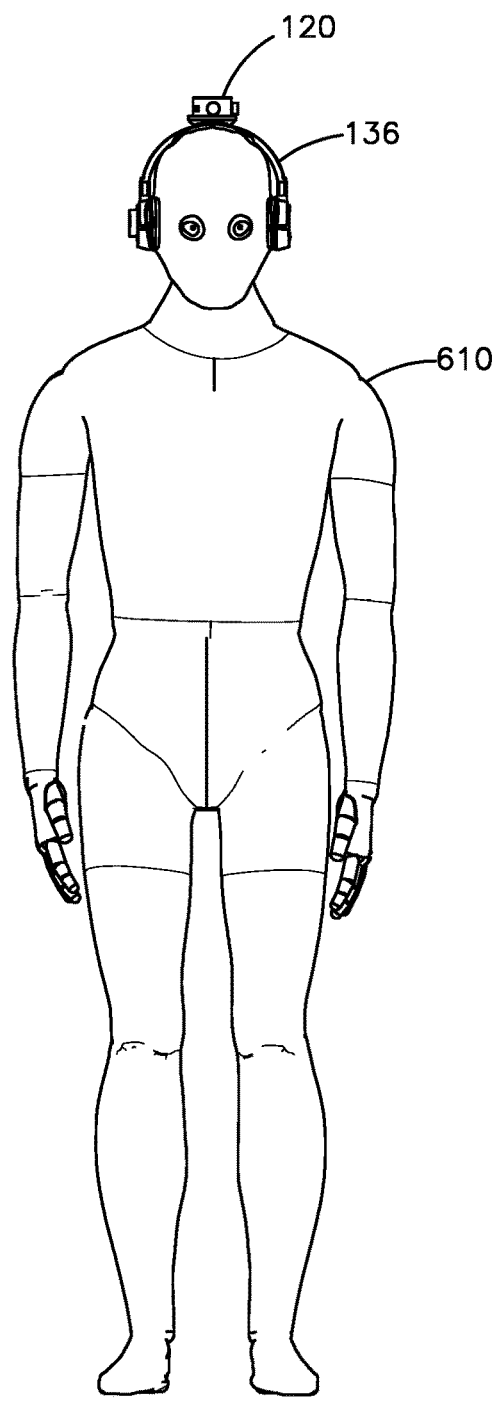

FIGS. 17A-B illustrate headset carrier 136 with sensor device 120 affixed thereto positioned on patient 610. As shown, headset carrier 136 has been positioned on the patient's head so that the arcuate shape of harness 1110 aligns with the crown of the patient's head. It will be appreciated that in the demonstrated scenario where sensor device 120 has been connected to rotation connector 1124 and headset carrier 136 has been positioned on the patient's head, a rotation sensor within sensor device 120 is positioned to measure cervical rotation.

Figure 18:
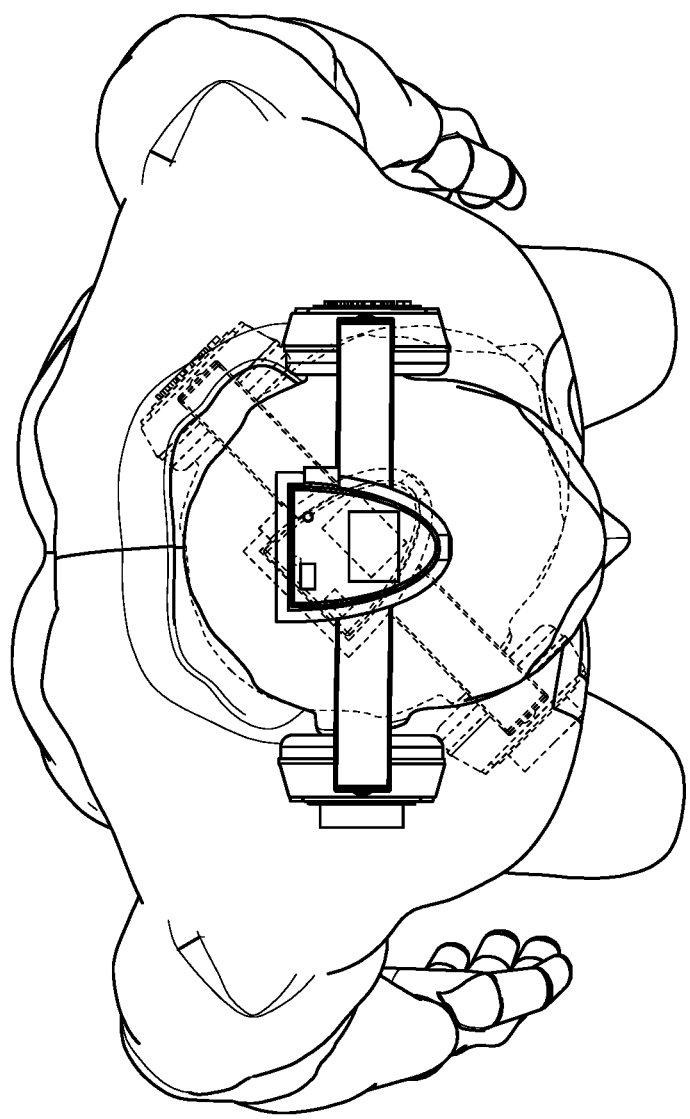
FIG. 18 depicts a view of a patient performing a movement for measurement by an example sensor device.

FIG. 18 illustrates a patient 610 with headset carrier 134 with sensor device 120 attached to rotation connector 1124 in preparation for measuring cervical rotation. In an example scenario, patient 610 begins the processing lying on his or her back with his or her forehead horizontal and head in a neutral position. The patient then rotates his or her head as far as possible to one side while keeping his or her shoulders still. Sensor device 120 is programmed to detect the degree of rotation. The patient then places his or head in a neutral position and rotates his or her head in the opposite direction. Sensor device 120 detects the maximum degree of rotation. Sensor device 120 stores the two rotational measurements and communicates the measurements to user system 150 where the measurement data is processed as described below.

Suspender Sensor System

FIGS. 19A-B depict suspender sensor system 140 which is used in taking lumbar flexion measurements. In other words, suspender sensor system 140 is used to collect measurements relating to the amount that the patient's lumbar area increases in length when the patient flexes forward from the waist. As shown, the suspender sensor system 140 has a configuration similar to a set of suspenders. Suspender sensor system 140 comprises a first band 1810 configured to be applied over a patient's first shoulder and affixed at one end to a garment proximate the patient's waist. Suspender sensor system 140 also comprises a second band 1812 configured to be applied over the patient's second shoulder and affixed at a first end to a garment proximate the patient's waist. Bands 1810 and 1812 are coupled at their second ends to third band 1820. Third band 1820 comprises at least a portion 1822 that is made of a flexible material and has stretch sensor 1824 integrated therewith. An end of third band 1820 is configured to be connected to a garment at the patient's waist. When a patient applies or attaches suspender sensor system 140, first band 1810 and second band 1812 are attached to a garment on the front of the patient's body and the bands extend over the patient's shoulders. Third band 1820 extends down the patient's back and is attached at an end to a garment at the patient's waist. Stretch sensor 1824 is programmed to derive a measurement of the amount that flexible portion 1822 is stretched. When the patient bends forward at his or her waist with knees fully extended, stretch sensor 1824 measures the amount that flexible portion 1822 expands. Stretch sensor 1824 records the measurements and communicates the measurements to user system 150 which initiated the measurement process.

Figure 20:
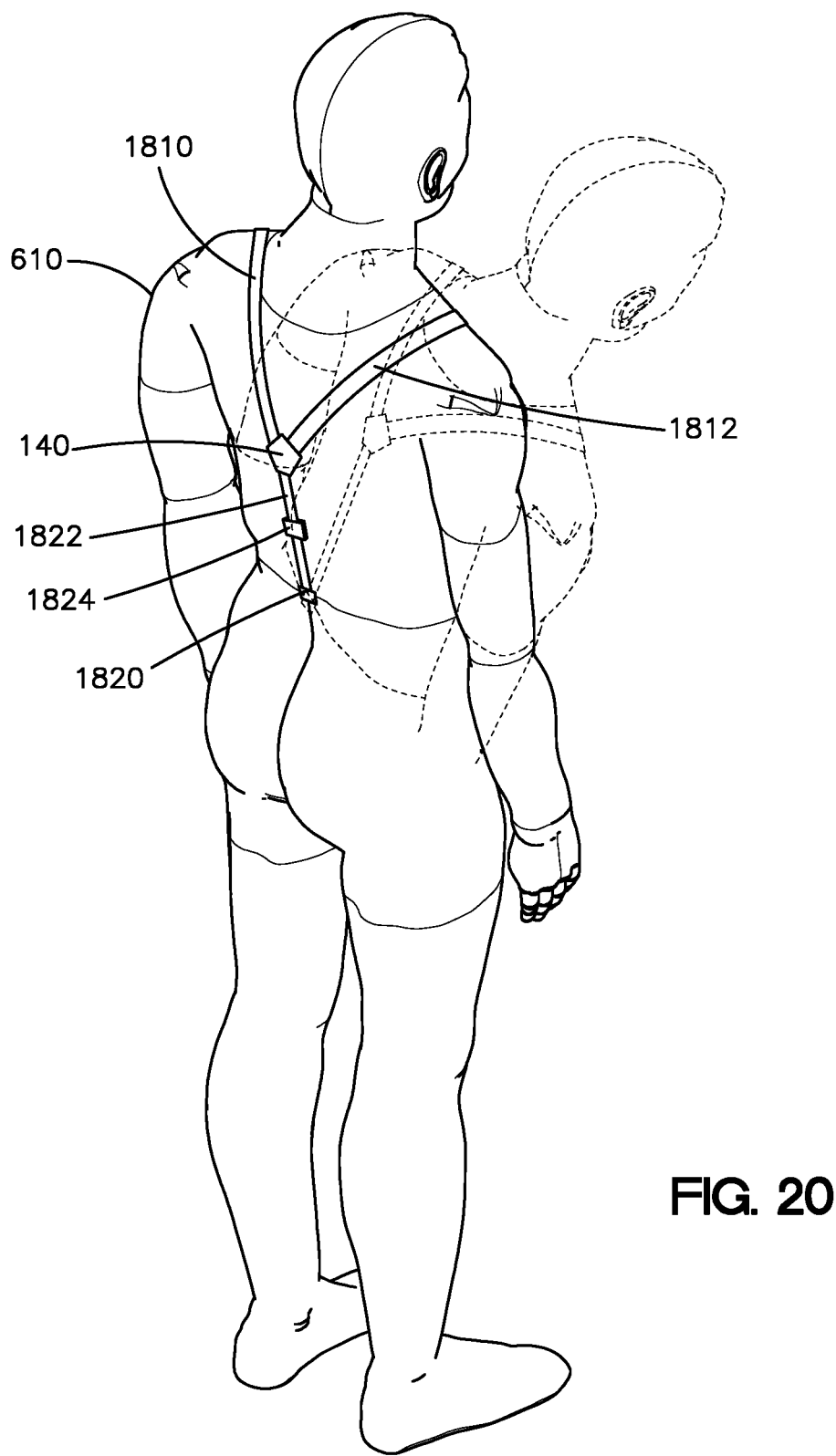
FIG. 20 depicts a view of a patient performing a movement for measurement by an example sensor device.

FIG. 20 illustrates suspender sensor system 140 positioned on patient 610. As shown, first band 1810 has been applied over a first shoulder, second band 1812 has been applied over the patient's second shoulder, and third band 1820 extends down the patient's back. As shown, patient 610 prepares for taking lumbar flexion measurements by standing in bare feet with the outer edges of the feet about 30 cm apart. The patient then flexes forward from the waist (as illustrated in dotted lines) as far as possible with knees fully extended. Stretch sensor 1824 measures the amount that the flexible portion 1822 extends or is stretched. Stretch sensor 1824 is programmed to store the measurement and communicate the measurement to user system 150.

Example Measurement Processing

Figure 21:
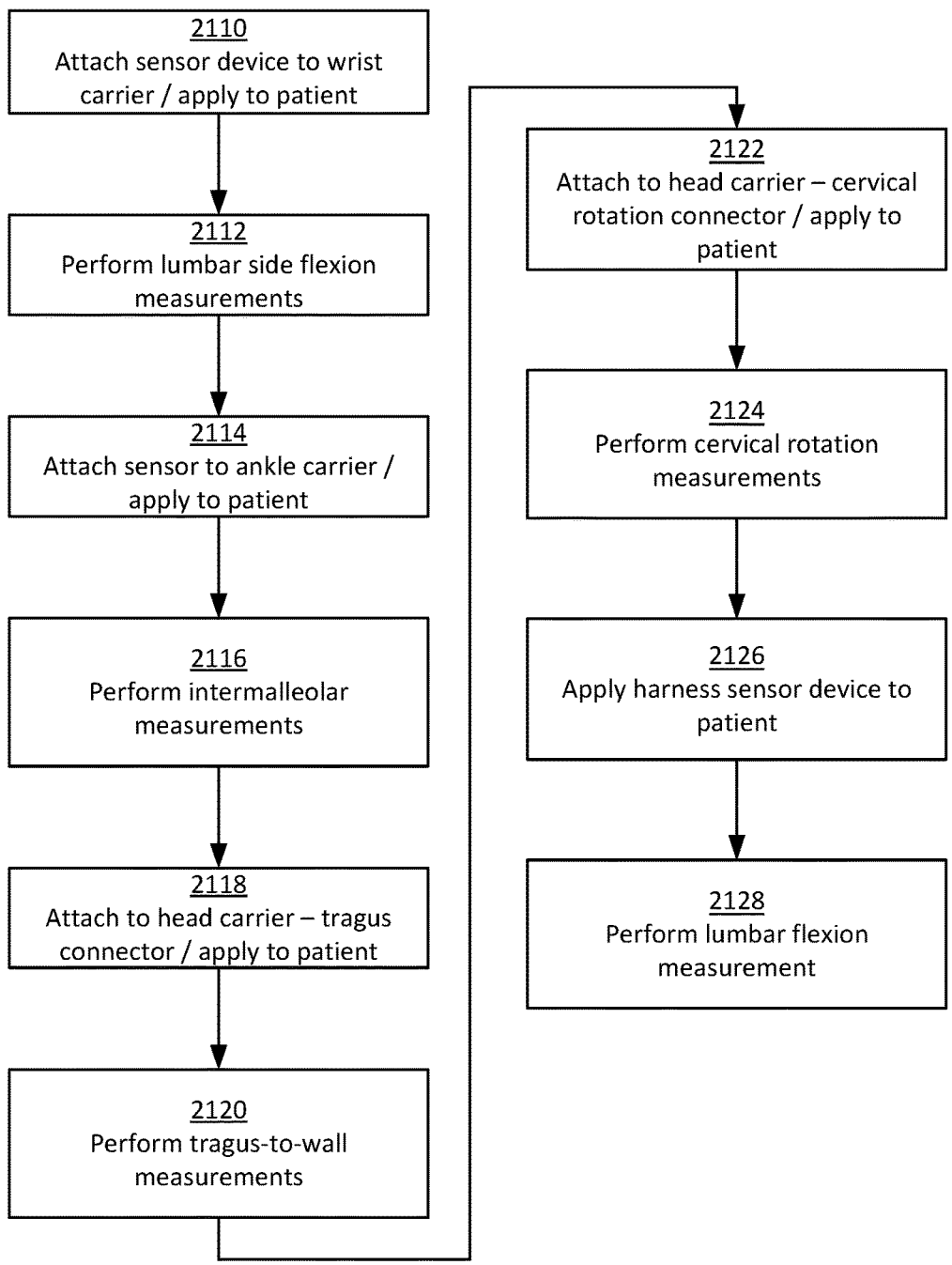
FIG. 21 depicts a flow diagram of an example method for gathering measurement data using example sensor device and carriers.

FIG. 21 depicts a flow chart of an example process for gathering measurements for use in generating a score such as, for example, a BASMI score using the disclosed system. Although the measurements are shown in a particular order, it will be understood that the order in which the measurements are performed can vary from the order shown. As shown, in an example process, at block 2110, the patient attaches sensor device 120 to wrist carrier 132 and applies the wrist carrier 132 to his or her wrist. At block 2112, sensor device 120 collects and records lumbar side flexion measurements as the patient performs the lumbar side flexion movements as described above.

At block 2114, the patient applies sensor device 120 to ankle carrier 134 and positions ankle carrier 134 adjacent to his foot and ankle. At block 2116, sensor device 120 collects and records intermalleolar measurements as the patient performs the intermalleaolar movements as described above.

At block 2118, the patient applies sensor device 120 to tragus connector 1120 of headset carrier 136 and positions headset carrier 136 on his or her head. At block 2120, sensor device 120 collects and records tragus-to-wall distance measurements as described above.

At block 2122, the patient attaches sensor device 120 to rotation connector 1124 of headset carrier 136 and positions headset carrier 136 on his or her head. At block 2124, sensor device 120 collects and records cervical rotation measurements as the patient performs the cervical rotation movements as described above.

At block 2126, the patient attaches suspender sensor device 140 to his or her torso. At block 2128, suspender sensor device 140 collects and records lumbar flexion measurements as the patient performs the lumbar flexion movements as described above.

The measurement data is transmitted by devices 120 and 140 to user computing device 150 where it is processed to determine a score which may be, for example a BASMI score.

Example Sensor Processing

Figure 22:
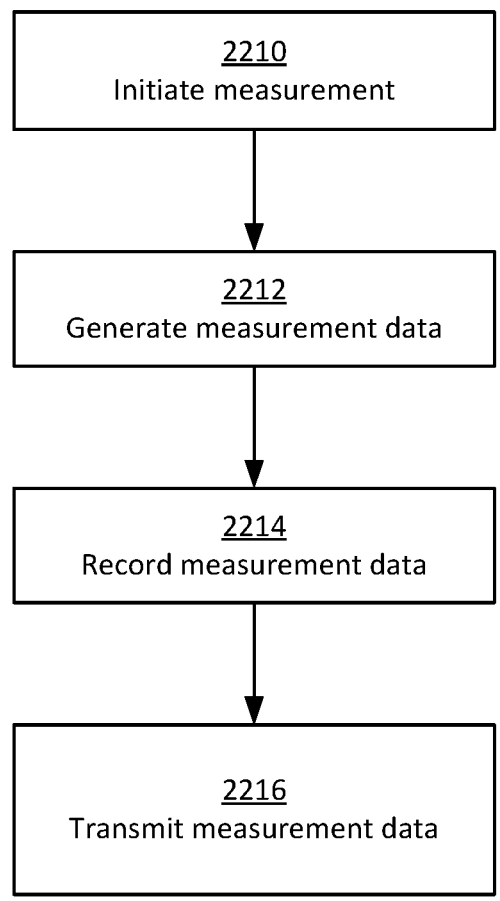
FIG. 22 depicts a flow diagram of example processing for gathering measurement data using an example sensor device and carriers.

FIG. 22 depicts a flow chart of example processing performed by sensor device 120 and stretch sensor 1824 during the measurement processing. Generally, the processing performed by sensor devices 120 and 1824 is performed in response to a request from user device 150 to perform the particular measurement. As shown, at block 2210, in response to a communication from user device 150, sensor device 120/1824 initiates measurement of the relevant movement. For example, where the measurement to be taken is lumbar side flexion, sensor device 120 initiates measurement of the distance between the sensor device and the floor. Where the measurement to be taken is a lumbar flexion, stretch sensor 1824 initiates measurement of the increase in lumbar length.

At block 2212, sensor device 120/1824 generates the measurement data. For example, where the measurement to be taken is tragus-to-wall, sensor device 120 measures the distance between sensor device 120 and the wall against which the patient is standing using one of the distance sensors embodiment in sensor device 120.

At block 2214, sensor device 120/1824 records the measurement data. For example, where the measurement taken is a lumbar flexion, stretch sensor 1824 records in memory the measured lumbar flexion length. In the example scenario wherein the measurement taken is intermalleolar distance, sensor device 120 records in its local memory the measured intermalleolar distance.

At block 2216, sensor device 120/1824 transmits the measurement data to user computing system 150 where the measurement may be processed and used in generating a composite score which may be, for example, a BASMI score.

Example User Device Processing

Figure 23:
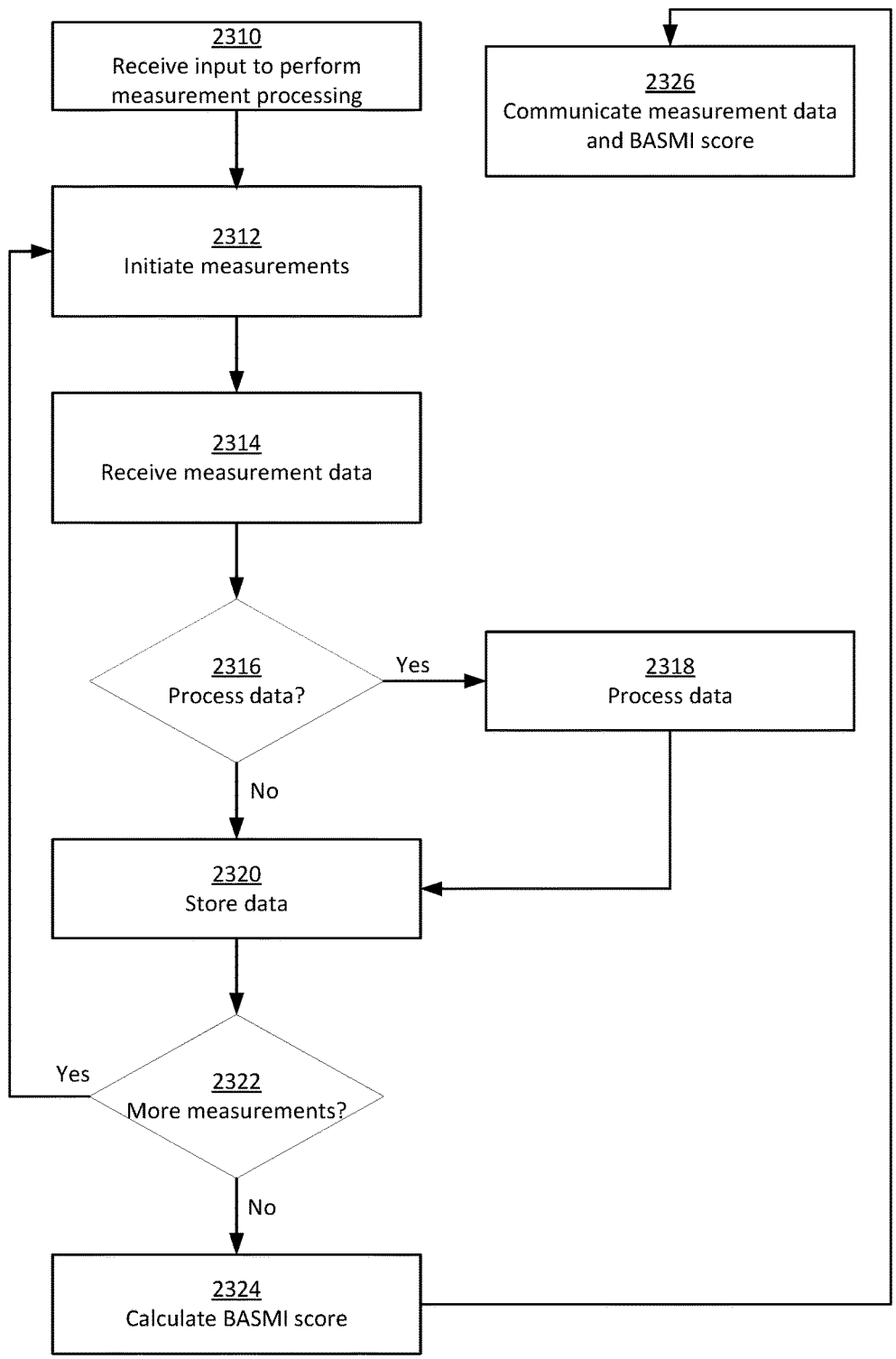
FIG. 23 depicts a flow diagram of example processing for gathering measurement data using an example sensor device and carriers.

User computing system 150 is programmed to initiate collection of measurements, record the measurements, and generate a score from the measurements. In an example embodiment, user computing system 150 is programmed to initiate collection of each of the five measurement types that are used in generating a BASMI score, to record the measurements, and generate the BASMI score. FIG. 23 depicts a flow chart of example processing performed by user computing system 150 in connection with generating a BASMI score. In an example embodiment, user computing system 150 is programmed to provide a graphical user interface with which the user/patient may select to initiate generating a BASMI score. As shown in FIG. 23, at block 2310, user computing system 150 receives input from a user, who may be the patient, specifying to generate a BASMI score.

After receiving the initial input indicating the user wishes to generate a BASMI score, user computing system 150 generates a user interface with which the user may specify the particular measurement that he or she is prepared to take. For example, the user may provide an input using the interface indicating that he or she is prepared to take a lumbar side flexion measurement. In an example scenario, the user may have previously attached sensor device 120 to wrist carrier 132 and is prepared to take the lumbar side flexion measurement.

In response to the input indicating the user is prepared, at block 2312, computing system 150 initiates the selected one of the five BASMI measurements by communicating to the appropriate one of sensor devices 120 and 1824 that the particular measurement should be taken. For example, in the scenario where the user selected to take a lumbar side flexion measurement, computing system 150 communicates to sensor device 120 to gather lumbar side measurements as the user/patient performs the required motions. In the scenario where the user selected to a lumbar flexion measurement, computing system 150 communicates to suspender sensor 140 to gather the lumbar flexion measurements as the user/patient performs the associated motion. Thereafter, the relevant sensor device records the measurements, stores the measurement data, and transmits the measurement data to user computing system 150.

At block 2314, user computing system 150 receives the measurement data from the sensor device 120, 140. The received data varies depending upon the particular type of measurement that was performed. In the scenario where the measurement was a lumbar side flexion measurement, two measurements, one for the left side and one for the right side, are received. Likewise, where the measurement is a tragus-to-wall measurement, two measurements, one for the left side and one for the right side, are received. Where the measurement is a cervical rotation measurement, two measurements, one for rotation to the left and one for rotation to the right, are received.

At block 2316, user computing system 150 determines whether processing of the received measurements is needed. For example, for tragus-to-wall, lumbar side flexion, and cervical rotation measurement data, further processing may be needed in order to generate an average of two received measurements (right and left). Further, for measurements such as tragus-to-wall and intermalleolar distance where the measurement taken was the distance between the sensor device and the particular object (wall in the case of tragus-to-wall and opposing ankle in intermalleolar distance), processing may be performed to account for the size of the sensor device in determining the actual distance. For example, it may be necessary to increase the measured distance in order to account for the size of the sensor device 120.

If at block 2316 user computing system 150 determines processing of the received measurement data is needed, at block 2318, user computing system 150 performs the relevant processing. Accordingly, in the case of tragus-to-wall measurements, user computing system 150 adds the length of the sensor device 120 itself, which may be, for example, approximately 5 cm, to the received distance measurements. User computing system 150 then averages the two measured values (one for left and one for right) to generate a tragus-to-wall value. In the instance where the received measurement data is an intermalleolar distance measurement, user computing system 150 adds the length of the sensor device 120 to the receive distance measurement to arrive at a processed intermalleolar distance. In the instance where the received measurement data is for lumbar side flexion and cervical rotation, computing system 150 averages the received two values (one for left and one for right) to generate a single processed value. After performing any needed processing, processing continues at block 2320.

At block 2320, user computing system 150 stores the measurement data and any processed measurement data in computing memory.

At block 2322, user computing system 150 determines whether there are further measurements to be taken. For example, in an example scenario, a first of the five BASMI measurements, for example, lumbar side flexion, may have been received. Accordingly, user computing system 150 determines that four measurements (tragus-to-wall, lumbar flexion, intermalleolar distance, and cervical rotation) still require to be taken. In another example scenario, two of the five BASMI measurements (lumbar side flexion and tragus-to-wall) may be been taken and received by user computing system 150. Accordingly, user computing system determines the three measurements (lumbar flexion, intermalleolar distance, and cervical rotation) that still require to be taken. Where additional measurements for creating a BASMI score are needed, computing system 150 may generate a user interface prompt for the user/patient to perform one of the outstanding measurements. In response to the prompt, user computing system 150 may receive an input selecting a particular measurement type. Processing then proceeds at block 2312, where in response to the selection, user computing system 150 initiates the selected measurement as described above.

If at block 2322, user computing system 150 determines that there are no additional measurements to be taken, i.e. all five of the BASMI measurements have been taken, processing continues at block 2324 where user computing system 150 calculates a BASMI score. In an example embodiment, calculating a BASMI score comprises user computing system 150 assigning an individual score ranging from 0 to 10 to each of the five measurements. The score is assigned based upon where the measured value falls within established intervals for each score type. The following chart illustrates an example set of intervals for each of the five BASMI measurement types.

|  | 0 | 1 | 2 | 3 | 4 | 5 | 6 | 7 | 8 | 9 | 10 |
|---|---|---|---|---|---|---|---|---|---|---|---|
| Tragus to wall (cm) | ≤10 | 10-12.9 | 13-15.9 | 16-18.9 | 19-21.9 | 22-24.9 | 25-27.9 | 28-30.9 | 31-33.9 | 34-36.9 | ≥37 |
| Lumbar Flexion (cm) | ≥7.0 | 6.4-7.0 | 5.7-6.3 | 5.0-5.6 | 4.3-4.9 | 3.6-4.2 | 2.9-3.5 | 2.2-2.8 | 1.5-2.1 | 0.8-1.4 | ≤0.7 |
| Intermalleolar distance (cm) | ≥120 | 110-119.9 | 100-109.9 | 90-99.9 | 80-89.9 | 70-79.9 | 60-69.9 | 50-59.9 | 40-49.9 | 30-39.9 | ≤30 |
| Cervical Rotation (degrees) | ≥85 | 76.6-85 | 68.1-76.5 | 59.6-68 | 51.1-59.5 | 42.6-51 | 34.1-42.5 | 25.6-34 | 17.1-25.5 | 8.6-17 | ≤8.5 |
| Lumbar Side Flexion (cm) | ≥20 | 18-20 | 15.9-17.9 | 13.8-15.8 | 11.7-13.7 | 9.6-11.6 | 7.5-9.5 | 5.4-7.4 | 3.3-5.3 | 1.2-3.2 | ≤1.2 |

The scores corresponding to each of the specified intervals are shown in the column header row. As shown, the score values range from zero to ten. User computing system 150 maintains in memory the noted intervals and corresponding score values. Accordingly, in the example scenario where the processed tragus-to-wall measurement is 14 cm, user computing system 150 assigns a score of 2 to the tragus-to-wall measurement. In the example scenario where the intermalleolar distance is 85 cm, user computing system 150 assigns a score of 4 to the intermalleolar distance measurement. User computing system 150 assigns a score to each of the of the five BASMI measurements. User computing system 150 then adds the values for the five scores and divides the sum by five. The result is the BASMI score for the particular individual based upon the recorded measurements. Generally, the higher the score on the BASMI index, the more severe the patient's limitation of movement.

Referring to FIG. 23, at block 2326, user computing system 150 stores the value and communicates the BASMI score. In an example embodiment, user computing system 150 displays the score on its user interface for review by the user/patient. Additionally, user computing system 150 transmits the BASMI score and related measurement data across network 112 to health records system 170. In an example embodiment, health records system 170 is programmed to store patients' health records including their BASMI scores and related BASMI measurements. Health records system 170 may be programmed to provide a service for storing and receiving health records.

User computing system 150 may be further programmed to communicate to a physician or health care provider computing system 180 that the patient has taken the BASMI measurements and a new BASMI score created. For example, user computing system 150 may generate an email or text to notify the physician or other health care professional of the new BASMI score records. In response to the notification or alert, the physician may access the health record computing system 170 in order to review the measurements and BASMI score. If necessary, the physician may follow up with the patient.

Example Processing Architecture

Figure 24:
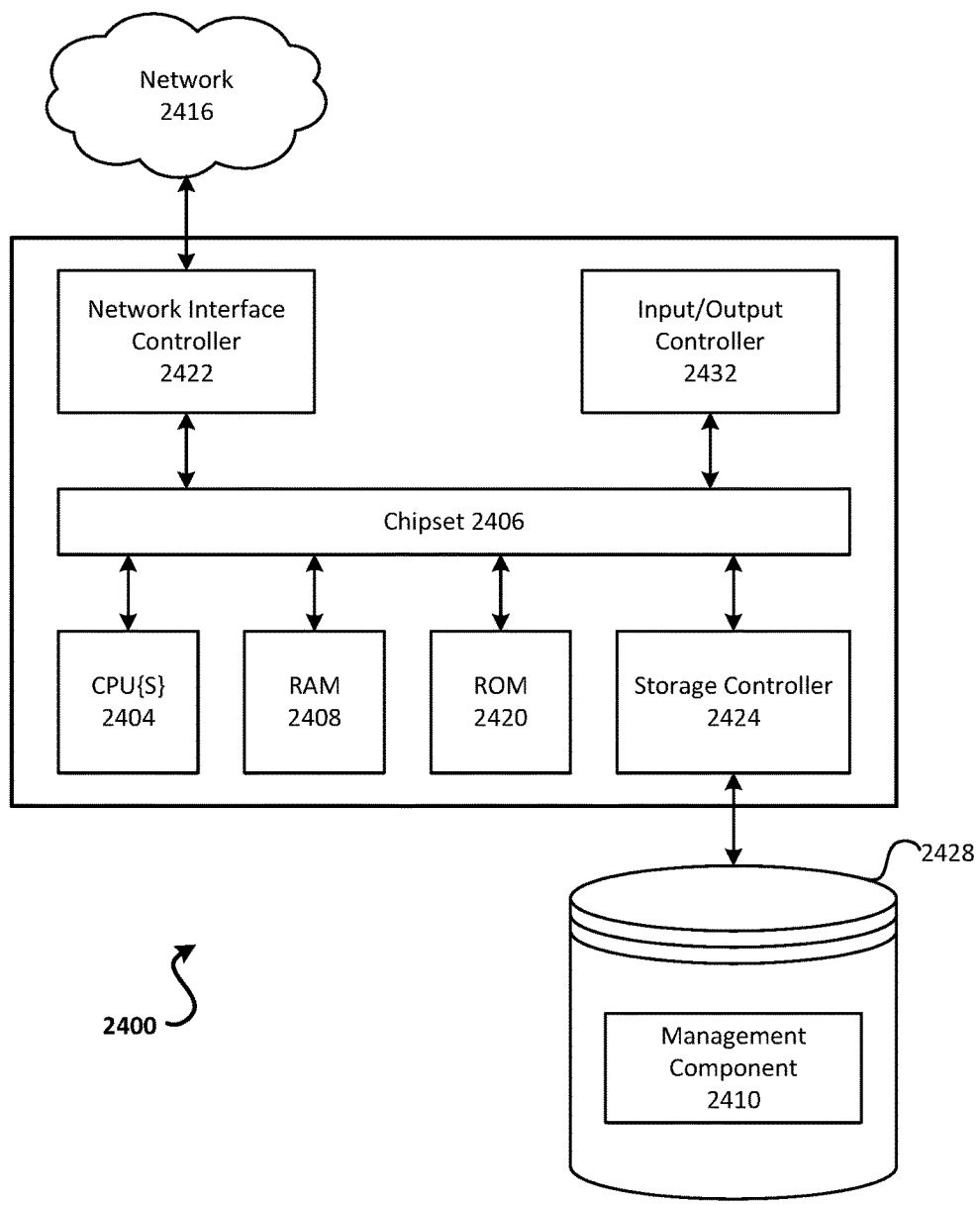
FIG. 24 depicts an example computing system.

FIG. 24 depicts an example computer architecture for a computing system 2300 capable of executing software for performing operations as described above including in connection with FIGS. 21 and 22. The computer architecture shown in FIG. 24 illustrates a conventional server computer, workstation, desktop computer, laptop, tablet, network appliance, PDA, e-reader, digital cellular phone, or other computing node, and may be utilized to execute any aspects of the software components presented herein described as executing on sensor devices 120, 1824, computing system 150, health records system 170, physician system 180, or on any other computing system mentioned herein.

Computer 2400 may include a baseboard, or "motherboard," which is a printed circuit board to which a multitude of components or devices may be connected by way of a system bus or other electrical communication paths. One or more central processing units (CPUs) 2404 may operate in conjunction with a chipset 2406. CPUs 2404 may be standard programmable processors that perform arithmetic and logical operations necessary for the operation of computer 2400.

CPUs 2404 may perform the necessary operations by transitioning from one discrete physical state to the next through the manipulation of switching elements that differentiate between and change these states. Switching elements may generally include electronic circuits that maintain one of two binary states, such as flip-flops, and electronic circuits that provide an output state based on the logical combination of the states of one or more other switching elements, such as logic gates. These basic switching elements may be combined to create more complex logic circuits including registers, adders-subtractors, arithmetic logic units, floating-point units, and the like.

Chipset 2406 may provide an interface between CPUs 2404 and the remainder of the components and devices on the baseboard. Chipset 2406 may provide an interface to a random access memory (RAM) 2408 used as the main memory in computer 2400. Chipset 2406 may further provide an interface to a computer-readable storage medium, such as a read-only memory (ROM) 2420 or non-volatile RAM (NVRAM) (not shown), for storing basic routines that may help to start up computer 2400 and to transfer information between the various components and devices. ROM 2420 or NVRAM may also store other software components necessary for the operation of computer 2400 in accordance with the embodiments described herein.

Computer 2400 may operate in a networked environment using logical connections to remote computing nodes and computer systems through network 2416. Chipset 2406 may include functionality for providing network connectivity through a network interface controller (NIC) 2422, such as a gigabit Ethernet adapter. NIC 2422 may be capable of connecting the computer 2400 to other computing nodes over network 2416. It should be appreciated that multiple NICs 2422 may be present in computer 2400, connecting the computer to other types of networks and remote computer systems.

Computer 2400 may be connected to a mass storage device 2428 that provides non-volatile storage for the computer. Mass storage device 2428 may store system programs, application programs, other program modules, and data, which have been described in greater detail herein. Mass storage device 2428 may be connected to computer 2400 through a storage controller 2424 connected to chipset 2406. Mass storage device 2428 may consist of one or more physical storage units. Storage controller 2424 may interface with the physical storage units through a serial attached SCSI (SAS) interface, a serial advanced technology attachment (SATA) interface, a fiber channel (FC) interface, or other type of interface for physically connecting and transferring data between computers and physical storage units.

Computer 2400 may store data on mass storage device 2428 by transforming the physical state of the physical storage units to reflect the information being stored. The specific transformation of a physical state may depend on various factors and on different implementations of this description. Examples of such factors may include, but are not limited to, the technology used to implement the physical storage units and whether mass storage device 2428 is characterized as primary or secondary storage and the like.

For example, computer 2400 may store information to mass storage device 2428 by issuing instructions through storage controller 2424 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. Computer 2400 may further read information from mass storage device 2428 by detecting the physical states or characteristics of one or more particular locations within the physical storage units.

In addition to mass storage device 2428 described above, computer 2400 may have access to other computer-readable storage media to store and retrieve information, such as program modules, data structures, or other data. It should be appreciated by those skilled in the art that computer-readable storage media can be any available media that provides for the storage of non-transitory data and that may be accessed by computer 2400.

By way of example and not limitation, computer-readable storage media may include volatile and non-volatile, transitory computer-readable storage media and non-transitory computer-readable storage media, removable and non-removable media implemented in any method or technology. Computer-readable storage media includes, but is not limited to, RAM, ROM, erasable programmable ROM (EPROM), electrically erasable programmable ROM (EEPROM), flash memory or other solid-state memory technology, compact disc ROM (CD-ROM), digital versatile disk (DVD), high definition DVD (HD-DVD), BLU-RAY, or other optical storage, magnetic cassettes, magnetic tape, magnetic disk storage, other magnetic storage devices, or any other medium that can be used to store the desired information in a non-transitory fashion.

Mass storage device 2428 may store an operating system utilized to control the operation of the computer 2400. According to one embodiment, the operating system comprises a version of the LINUX operating system. According to another embodiment, the operating system comprises a version of the WINDOWS SERVER operating system from the MICROSOFT Corporation. According to further embodiments, the operating system may comprise a version of the UNIX operating system. It should be appreciated that other operating systems may also be utilized. Mass storage device 2428 may store other system or application programs and data utilized by computer 2400, such as management component 2410 and/or the other software components described above.

Mass storage device 2428 or other computer-readable storage media may also be encoded with computer-executable instructions, which, when loaded into computer 2400, transforms the computer from a general-purpose computing system into a special-purpose computer capable of implementing the embodiments described herein. These computer-executable instructions transform computer 2400 by specifying how CPUs 2404 transition between states, as described above. Computer 2400 may have access to computer-readable storage media storing computer-executable instructions, which, when executed by computer 2400, may perform operating procedures described above in connection with FIGS. 22 and 23.

Computer 2400 may also include an input/output controller 2432 for receiving and processing input from a number of input devices, such as a keyboard, a mouse, a touchpad, a touch screen, an electronic stylus, or other type of input device. Similarly, input/output controller 2432 may provide output to a display, such as a computer monitor, a flat-panel display, a digital projector, a printer, a plotter, or other type of output device. It will be appreciated that computer 2400 may not include all of the components shown in FIG. 24, may include other components that are not explicitly shown in FIG. 24, or may utilize an architecture completely different than that shown in FIG. 24.

Accordingly, Applicant has disclosed systems comprising sensor devices that may be affixed to a patient and used to perform clinical measurements such as, for example, measurements for calculating a BASMI score. A first sensor device is configured to be successively attached to each of a wrist carrier, an ankle carrier, and a headset carrier. The carriers are attached to, or positioned next to, the relevant portion of the patient's body in order to perform particular measurements. As the patient performs the routine of motions, the sensor device records the measurements and communicates the measurements to a user computing device. A second sensor device is configured to be applied to the patient's torso and an additional measurement of patient flexibility taken and communicated to the user computing device. The user computing device generates a score from the recorded measurements.

It will be appreciated that while example embodiments have been described in connection with taking measurements relating to ankylosing spondylitis, the intended embodiments extend to taking measurements and generating scores for any suitable purpose and/or in connection with any medical condition. For example, the disclosed embodiments may be used in connection with taking measurements relating to tracking progress of a patient recovering from surgery. Likewise, while the disclosed embodiments have described using the example of generating a BASMI score, the disclosed embodiments may be used in connection with taking measurements associated with any suitable methodology or index. For example, the disclosed concepts may be used in connection with taking measurements for use in connection with the evaluating a patient using any of the following: Bath Ankylosing Spondylitis Disease Activity Index; Ankylosing Spondylitis Disease Activity Score; and Bath Ankylosing Spondylitis Global Score.

It will be appreciated that the disclosed systems and methods allow patients to take clinical measurements by themselves and within the comfort of their own home. Accordingly, the disclosed systems remove impediments to taking the clinical measurements more frequently than is currently the practice. As a result, patients receive better care.

It should be appreciated that the subject matter presented herein may be implemented as a computer process, a computer-controlled apparatus, or a computing system or an article of manufacture, such as a computer-readable storage medium. While the subject matter described herein is presented in the general context of program modules that execute on one or more computing devices, those skilled in the art will recognize that other implementations may be performed in combination with other types of program modules. Generally, program modules include routines, programs, components, data structures, and other types of structures that perform particular tasks or implement particular abstract data types.

Those skilled in the art will also appreciate that the subject matter described herein may be practiced on or in conjunction with other computer system configurations beyond those described herein, including multiprocessor systems, microprocessor-based or programmable consumer electronics, minicomputers, mainframe computers, handheld computers, personal digital assistants, e-readers, cellular telephone devices, special purposed hardware devices, network appliances, and the like. The embodiments described herein may also be practiced in distributed computing environments, where tasks are performed by remote processing devices that are linked through a communications network. In a distributed computing environment, program modules may be located in both local and remote memory storage devices.

It will be appreciated that while illustrative embodiments have been disclosed, the scope of potential embodiments is not limited to those explicitly described. For example, while the concepts are described with reference to requests received to perform particular types of functions or commands, the envisioned embodiments extend to processing involving any and all types of functions and commands. Similarly, while the concepts are described with reference to particular protocols and formats, the envisioned embodiments extend to processing involving any and all types of protocols and formats.

Each of the processes, methods, and algorithms described in the preceding sections may be embodied in, and fully or partially automated by, code modules executed by one or more computers or computer processors. The code modules may be stored on any type of non-transitory computer-readable medium or computer storage device, such as hard drives, solid state memory, optical disc, and/or the like. The processes and algorithms may be implemented partially or wholly in application-specific circuitry. The results of the disclosed processes and process steps may be stored, persistently or otherwise, in any type of non-transitory computer storage such as, e.g., volatile or non-volatile storage.

The various features and processes described above may be used independently of one another, or may be combined in various ways. All possible combinations and subcombinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example embodiments. The example systems and components described herein may be configured differently than described. For example, elements may be added to, removed from or rearranged compared to the disclosed example embodiments.

It will also be appreciated that various items are illustrated as being stored in memory or on storage while being used, and that these items or portions of thereof may be transferred between memory and other storage devices for purposes of memory management and data integrity. Alternatively, in other embodiments some or all of the software modules and/or systems may execute in memory on another device and communicate with the illustrated computing systems via inter-computer communication. Furthermore, in some embodiments, some or all of the systems and/or modules may be implemented or provided in other ways, such as at least partially in firmware and/or hardware, including, but not limited to, one or more application-specific integrated circuits (ASICs), standard integrated circuits, controllers (e.g., by executing appropriate instructions, and including microcontrollers and/or embedded controllers), field-programmable gate arrays (FPGAs), complex programmable logic devices (CPLDs), etc. Some or all of the modules, systems and data structures may also be stored (e.g., as software instructions or structured data) on a computer-readable medium, such as a hard disk, a memory, a network, or a portable media article to be read by an appropriate drive or via an appropriate connection. The systems, modules, and data structures may also be transmitted as generated data signals (e.g., as part of a carrier wave or other analog or digital propagated signal) on a variety of computer-readable transmission media, including wireless-based and wired/cable-based media, and may take a variety of forms (e.g., as part of a single or multiplexed analog signal or as multiple discrete digital packets or frames). Such computer program products may also take other forms in other embodiments. Accordingly, the present invention may be practiced with other computer system configurations.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While certain example embodiments have been described, these embodiments have been presented by way of example only and are not intended to limit the scope of the inventions disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions, and changes in the form of the methods and systems described herein may be made without departing from the spirit of the inventions disclosed herein. The accompanying claims and their equivalents are intended to cover such forms or modifications as would fall within the scope and spirit of certain of the inventions disclosed herein.

What is claimed:

1. A system, comprising:
a sensor device comprising:
a first sensor configured to measure distance;
a second sensor configured to measure rotation; and
one or more sensor device connectors configured to selectively attach the sensor device to a first carrier, a second carrier, and a third carrier, wherein;
the first carrier comprises a first connector configured to interconnect with one of the one or more sensor device connectors, the first carrier configured to be attached to a human arm or hand;
the second carrier comprises a second connector configured to interconnect with one of the one or more sensor device connectors, the second carrier configured to be applied to a human ankle; and
the third carrier comprises at least a third connector configured to interconnect with one of the one or more sensor device connectors, the third carrier configured to be attached to a human head; and
a computing device configured to communicate with the sensor device and comprising a computing processor and computing memory, the computing memory comprising executable instructions that when executed cause the computing processor to perform operations comprising:
receiving a first user input indicating that the sensor device is attached to the first carrier and indicating that the first carrier is attached to the human arm or hand, whereby the sensor device is attached to the human arm or hand;
initiating measurement by the sensor device such that the sensor device generates first measurement data while the sensor device is attached to the first carrier and the first carrier is attached to the human arm or hand, in response to the first user input;
receiving the first measurement data from the sensor device;
receiving a second user input indicating that the sensor device is attached to the second carrier and indicating that the second carrier is applied to the human ankle;
initiating measurement by the sensor device such that the sensor device generates second measurement data while the sensor device is attached to the second carrier and the second carrier is applied to the human ankle, in response to the second user input;
receiving the second measurement data from the sensor device;
receiving a third user input indicating that the sensor device is attached to the third carrier and indicating that the third carrier is attached to the human head, whereby the sensor device is attached to the human head;
initiating measurement by the sensor device such that the sensor device generates third measurement data while the sensor device is attached to the third carrier and the third carrier is attached to the human ankle, in response to the third user input; and
receiving the third measurement data from the sensor device.

2. The system of claim 1, wherein the sensor device comprises:
a casing, the casing comprising:
a first connector configured to mate the sensor device with at least one carrier of the first, second, and third carriers, the first connector positioned relative to the first sensor such that the first sensor is positioned to measure distance when the first connector is mated with the at least one carrier; and
a second connector configured to mate the sensor device with at least one other carrier of the first, second, and third carriers, the second connector positioned relative to the second sensor such that the second sensor is positioned to measure rotation when the second connector is mated with the at least one other carrier.

3. The system of claim 1, wherein the first sensor comprises a sensor that employs ultrasonic waves to determine distance.

4. The system of claim 1, wherein the first sensor comprises a sensor that employs reflected light to determine distance.

5. The system of claim 2, wherein the sensor device comprises the first sensor configured to measure distance and another sensor configured to measure distance, wherein:
the first sensor employs ultrasonic waves to determine distance and is positioned proximate a first end of the sensor device; and
the other sensor employs reflected light to determine distance.

6. The system of claim 5,
wherein the casing has a first aperture at the first end of the sensor device, the first sensor being positioned proximate the first aperture, and
wherein the casing has a second aperture at the second end of the sensor device, the other sensor being positioned proximate the second aperture.

7. The system of claim 1, wherein the sensor device comprises:
a wireless communication processor programmed to communicate data to and from the sensor device; and
a computing processor communicatively coupled to the first sensor, the second sensor, and the wireless communication processor, the computing processor comprising executable instructions that, when executed, cause the computing processor to perform operations comprising:
initiate performing measurements by the first sensor and the second sensor;
receive data relating to measurements from the first sensor and the second sensor; and
initiate communication of the data relating to measurements by the wireless communication processor.

8. The system of claim 1, wherein the first carrier further comprises a strap, the first connector is secured to the strap, and the strap is sufficiently long to wrap around a human arm or hand.

9. The system of claim 8, wherein the strap and first connector are positioned relative to each other such that when the one or more sensor device connectors is connected to the first connector and the first carrier is applied to a human arm or hand, the first sensor is positioned to measure distance from a surface on which a human to whose arm or hand the first carrier is attached is standing.

10. The system of claim 1, wherein the second carrier comprises a frame, the second connector is affixed to the frame, and the frame is shaped to be positioned adjacent to a human ankle.

11. The system of claim 1, wherein the third carrier comprises a harness configured to be positioned on a human head.

12. The system of claim 11, wherein the third connector is attached to the harness such that when the one or more sensor device connectors is connected to the third connector and the harness is positioned on a human head, the second sensor is positioned to measure rotation of the human head from side to side.

13. The system of claim 11, wherein the third connector is attached to the harness such that when the one or more sensor device connectors is connected to the third connector and the harness is positioned on a human head, the first sensor is positioned to measure distance from proximate a human ear to a surface.

14. The system of claim 1, further comprising:
a suspender sensor system comprising:
a first band configured to be received over a first human shoulder and affixed at a first end to a garment proximate a waist of a human;
a second band configured to be received over a second human shoulder and affixed at a first end to a garment proximate the waist; and
a second sensor device comprising third band, the third band coupled in a fixed position relative to a second end of the first band and a second end of the second band, the third band made from an elastic material, and the second sensor device programmed to measure a length that the third band is stretched.

15. The system of claim 1, wherein the computing memory comprising executable instructions that when executed cause the computing processor to perform further operations comprising:
activating, in response to the first user input, the sensor device to measure distance from a surface on which a human to whose arm or hand the first carrier is attached is standing, wherein the first measurement data comprises a measurement of distance from a surface on which the human to whose arm or hand the first carrier is attached is standing
activating the sensor device, in response to the second user input, to measure distance from an opposing ankle of the human to whose ankle the second carrier is adjacent, wherein the second measurement data comprises a measurement of distance from an opposing ankle of the human to whose ankle the second carrier is adjacent
activating the sensor device, in response to the third user input, to measure rotation of a human head from side to side, wherein the third measurement data comprises a measurement of rotation of a human head from side to side
activating the sensor device, in response to a fourth user input, to measure distance from proximate a human ear to a surface; and
receiving from the sensor device a fourth measurement data that comprises a measurement of distance from proximate a human ear to a surface.

16. The system of claim 15, wherein the computing memory comprising executable instructions that when executed cause the computing processor to perform further operations comprising:
generating a first BASMI score for the received measurement of distance from a surface in which a human to whose arm or hand the first carrier is attached is standing;
generating a second BASMI score for the received measurement of distance from an opposing ankle of the human to whose ankle the second carrier is adjacent;
generating a third BASMI score for the received measurement of rotation of a human head from side to side; and
generating a fourth BASMI score for the received measurement of distance from proximate a human ear to a surface.

17. The system of claim 16, the computing memory comprising executable instructions that when executed cause the computing processor to perform further operations comprising:
activating a second sensor device to measure a length that a third band is stretched in response to the human bending forward; and
generating a fifth BASMI score of the measured length that the third band is stretched.

18. The system of claim 1, wherein the first, second, and third carriers are different from one another, such that none of the first, second, and third carriers are identical to one another.

19. The system of claim 1, wherein the second carrier comprises a bottom portion configured to abut a portion of a patient's foot, and a second portion that extends substantially upwards away from the bottom portion and adjacent to the patient's ankle, the second portion supporting the second connector.

20. The system of claim 1, wherein a single connector of the sensor device selectively attaches the sensor device to each of the first, second, and third carriers.

21. The system of claim 1, wherein the first measurement data represents lumbar side flexion measurements of a patient, wherein the second measurement data represents intermalleolar measurements of the patient, and wherein the third measurement data represents tragus-to-wall distance or cervical spine rotation measurements of the patient.

22. The system of claim 21, wherein the computing memory comprising executable instructions that when executed cause the computing processor to perform further operations comprising calculating a BASMI score based on the first measurement data, the second measurement data, and the third measurement data.

23. The system of claim 21, wherein the computing memory comprising executable instructions that when executed cause the computing processor to perform further operations comprising generating a first prompt on a user interface for a user to provide the first user input, generating a second prompt on the user interface for the user to provide the second user input, and generating a third prompt on the user interface for the user to provide the third user input.

* * * * *